(12) United States Patent
Kono et al.

(10) Patent No.: US 7,945,108 B2
(45) Date of Patent: May 17, 2011

(54) MICROSCOPE APPARATUS CONTROL METHOD AND MICROSCOPE APPARATUS

(75) Inventors: Takayuki Kono, Tokyo (JP); Akihiko Yoshikawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 942 days.

(21) Appl. No.: 11/893,823

(22) Filed: Aug. 17, 2007

(65) Prior Publication Data

US 2008/0055718 A1    Mar. 6, 2008

(30) Foreign Application Priority Data

Sep. 6, 2006    (JP) ................... 2006-241783

(51) Int. Cl.
*G06K 9/40* (2006.01)
*G02B 21/26* (2006.01)
*G01N 21/76* (2006.01)

(52) U.S. Cl. .................. 382/255; 359/391; 436/172

(58) Field of Classification Search .......... 382/128–134, 382/255, 312; 359/381, 382, 283, 385, 391; 356/300, 400; 436/172, 525, 805
See application file for complete search history.

(56) References Cited

U.S. PATENT DOCUMENTS

| | | | |
|---|---|---|---|
| 6,433,325 B1 | 8/2002 | Trigg | |
| 6,898,004 B2 * | 5/2005 | Shimizu et al. | 359/385 |
| 6,980,293 B1 * | 12/2005 | Harada | 356/317 |
| 7,224,826 B2 * | 5/2007 | Shibazaki et al. | 382/128 |
| 7,277,566 B2 * | 10/2007 | Miyawaki et al. | 382/128 |
| 7,285,787 B2 * | 10/2007 | Horigome et al. | 250/400 |
| 7,415,144 B2 * | 8/2008 | Imaizumi et al. | 382/128 |
| 7,564,623 B2 * | 7/2009 | Vodyanoy et al. | 359/385 |
| 7,611,907 B2 * | 11/2009 | Dickson et al. | 436/525 |
| 7,649,684 B2 * | 1/2010 | Kawasaki et al. | 359/385 |
| 7,867,752 B1 * | 1/2011 | Greenberger et al. | 435/286.1 |
| 2002/0090127 A1 | 7/2002 | Wetzel et al. | |
| 2002/0177149 A1 | 11/2002 | Rimm et al. | |
| 2003/0103662 A1 | 6/2003 | Finkbeiner | |
| 2004/0047033 A1 | 3/2004 | Nakagawa | |
| 2008/0013816 A1 | 1/2008 | Rimm et al. | |

FOREIGN PATENT DOCUMENTS

| | | |
|---|---|---|
| JP | 11-202213 A | 7/1999 |
| JP | 2006-506672 A | 2/2006 |
| WO | WO 02/086498 A1 | 10/2002 |

OTHER PUBLICATIONS

An Extended European Search Report dated Jul. 24, 2008, issued in a counterpart European Application.

* cited by examiner

*Primary Examiner* — Kanji Patel
(74) *Attorney, Agent, or Firm* — Holtz, Holtz, Goodman & Chick, PC

(57) ABSTRACT

The present invention provides a control method for a microscope apparatus, comprising: a first step for recognizing a type of a specimen retention member retaining a specimen; a second step for obtaining a first image including the whole image of a specimen retention member showing a picture of the entirety of the specimen retention member and an image of the specimen, and obtaining a second image including only the whole image of the specimen retention member in accordance with the type of the specimen retention member; and a third step for obtaining a macro observation image with a self fluorescence removed except for the specimen based on the first image and second image.

22 Claims, 15 Drawing Sheets

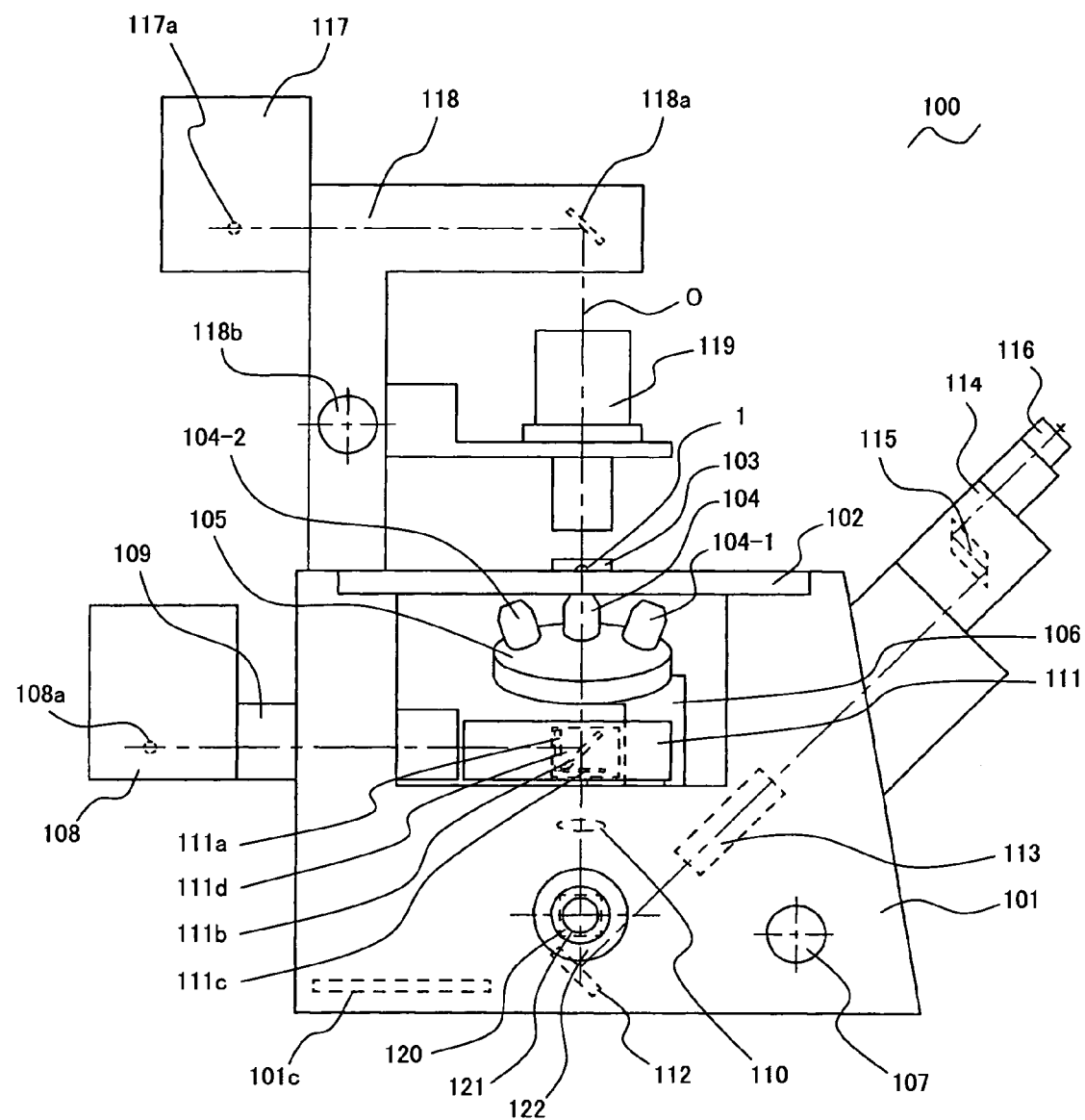
F I G. 1

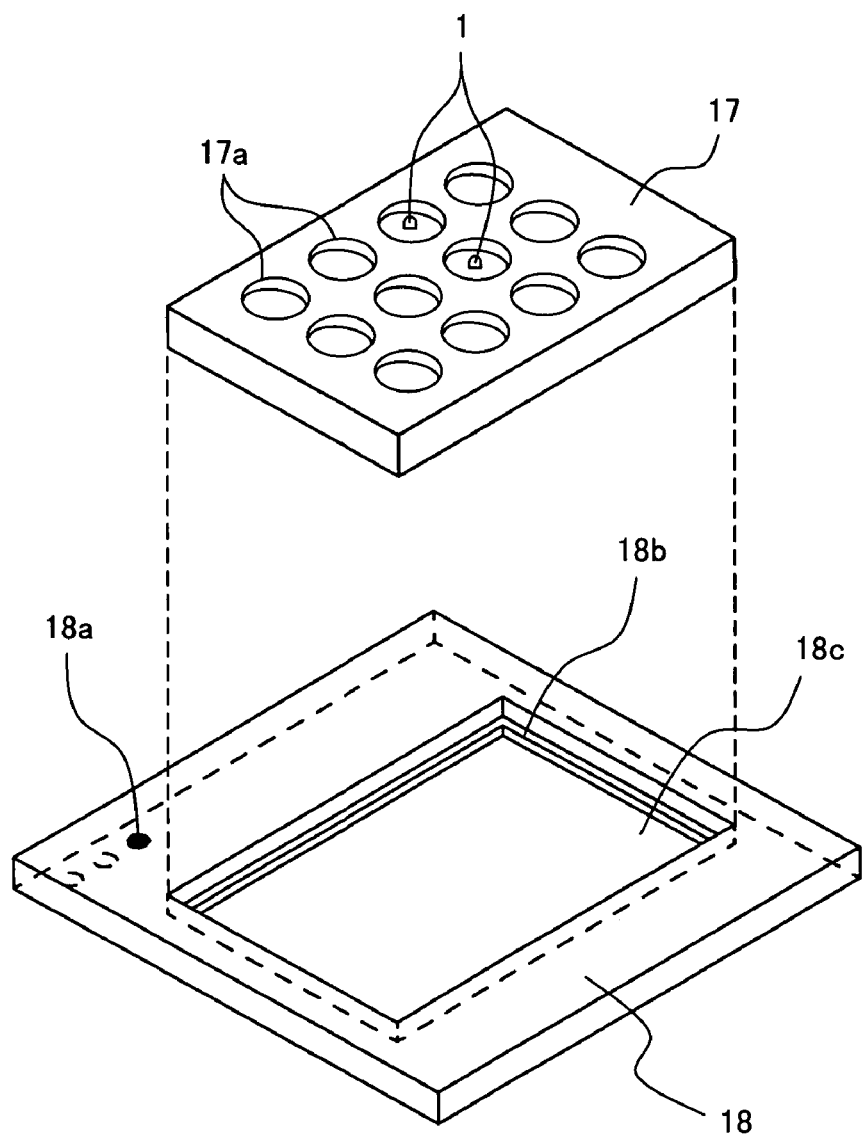
F I G. 3

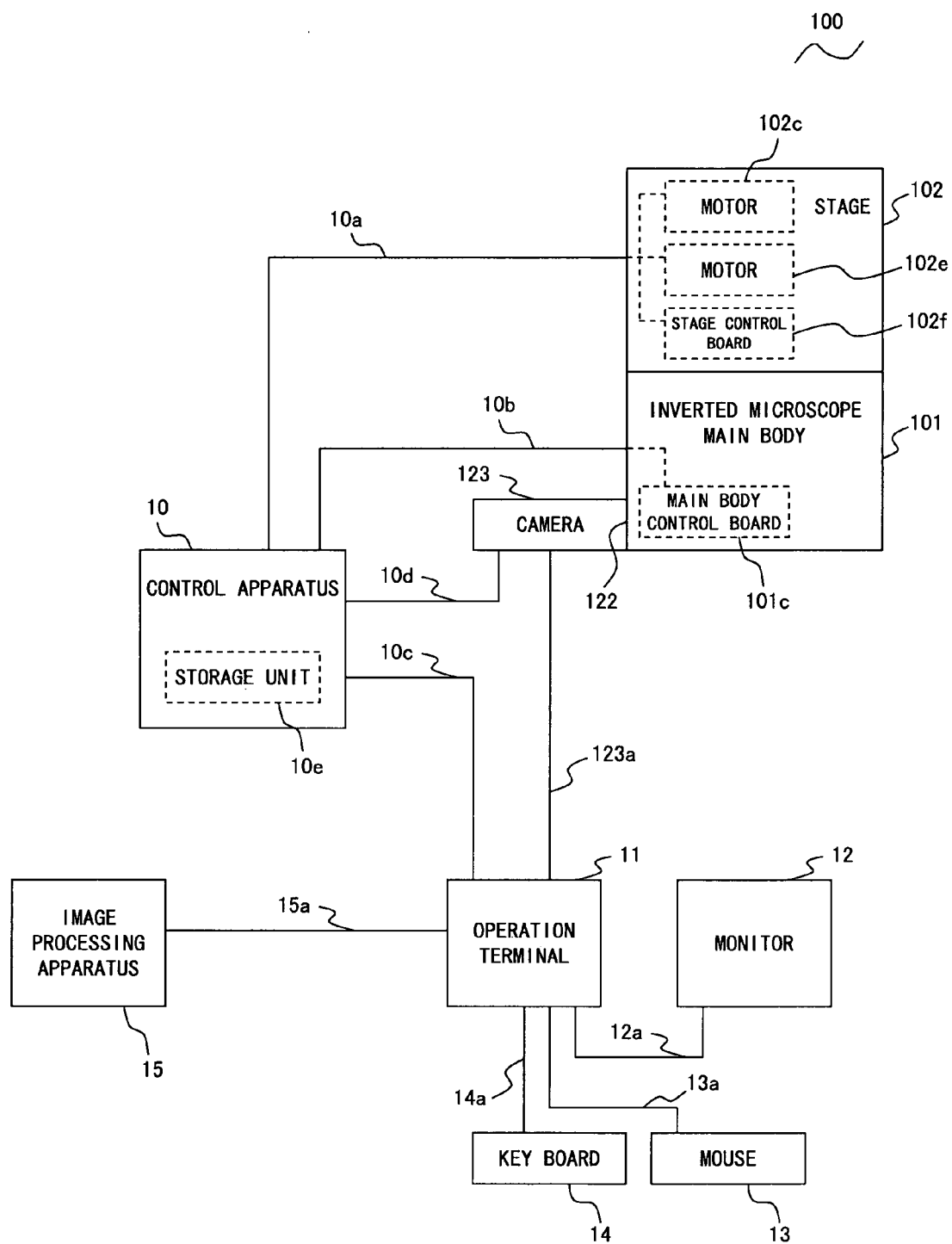
F I G. 5

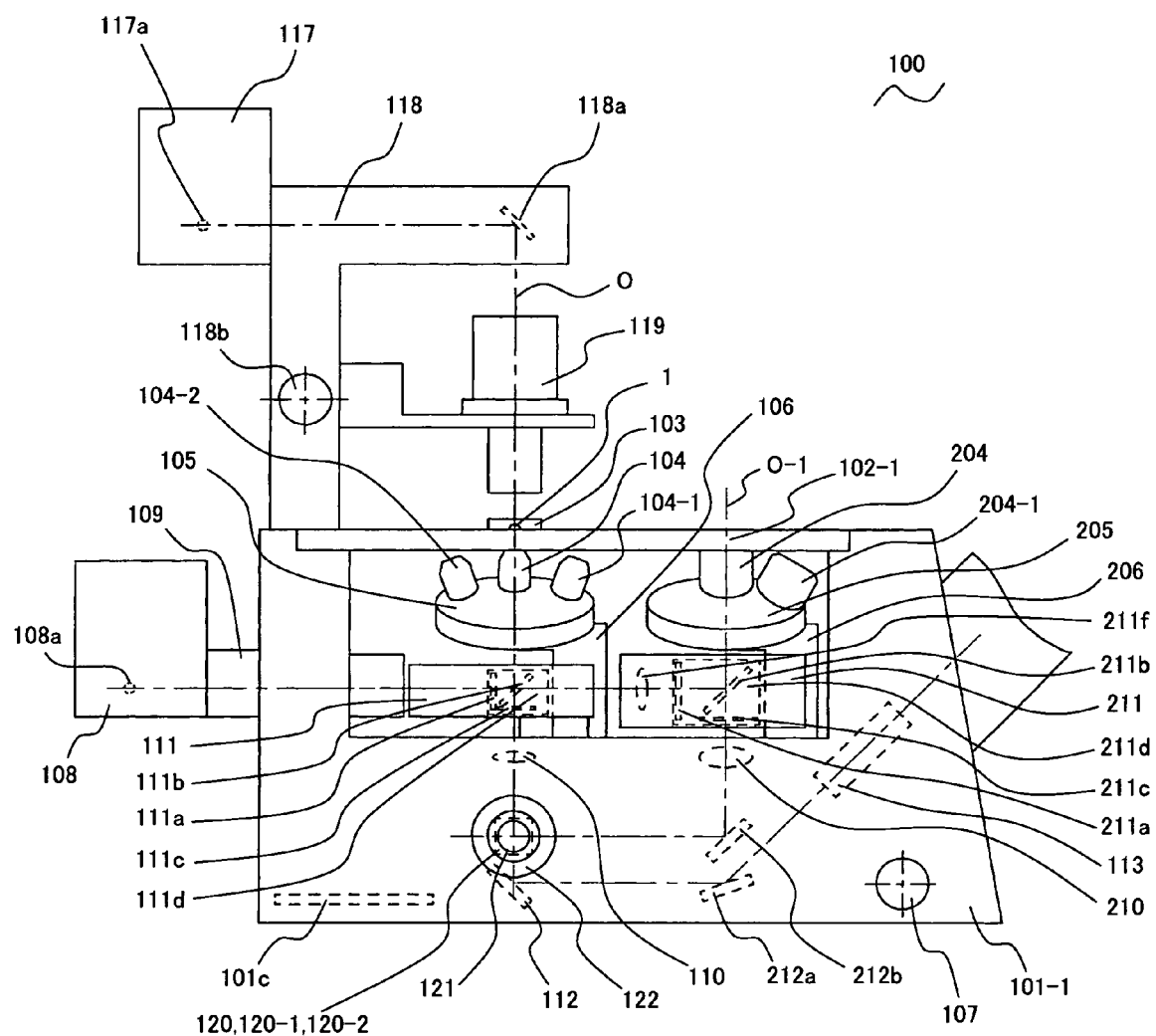
F I G. 1 2

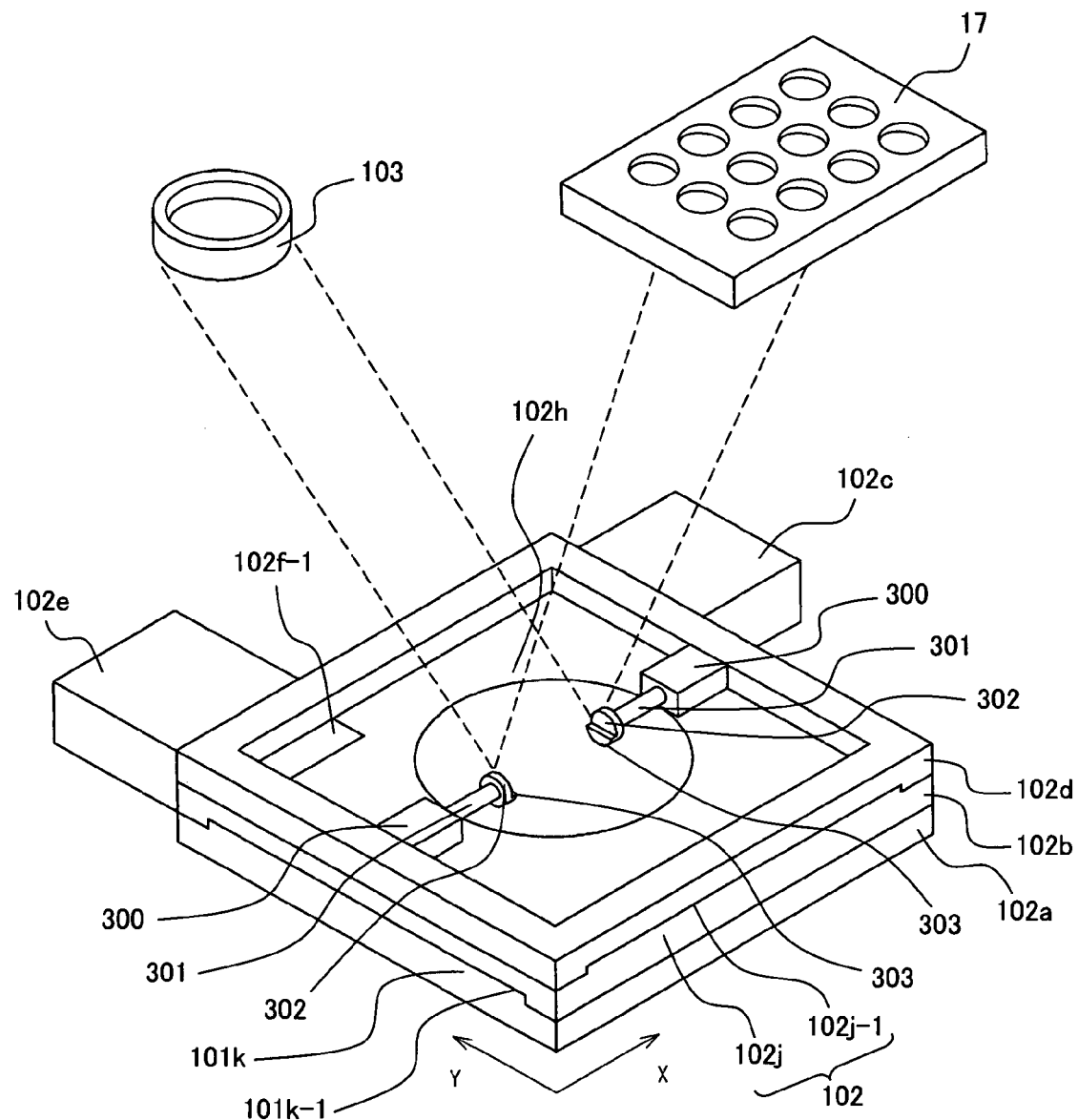
F I G. 14

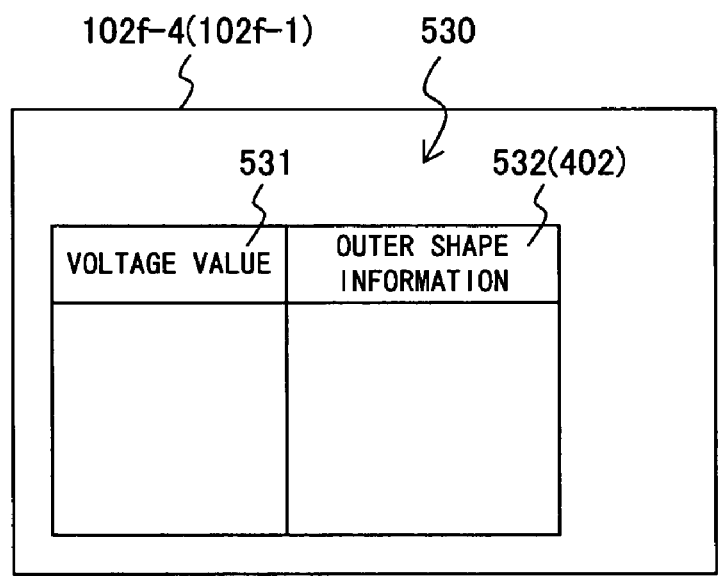
F I G. 1 5

MICROSCOPE APPARATUS CONTROL METHOD AND MICROSCOPE APPARATUS

CROSS REFERENCE TO RELATED APPLICATIONS

This application is based upon and claims the benefit of priority from the prior Japanese Patent Application No. 2006-241783, filed Sep. 6, 2006, the entire contents of which are incorporated herein by reference.

BACKGROUND OF THE INVENTION

1. Field of the Invention

The present invention relates to a microscope apparatus and control technique for the same, and for example to a microscope apparatus comprising a specimen retention member holder.

2. Description of the Related Art

In recent years, when observing a specimen such as a cell, a fluorescent observation by using a microscope is used. In such a case, usually performed are a cultivation of a cell in a Petri dish and an observation of a specific region of the cell. Also performed is a cultivation of cells in a plurality of wells of a well plate followed by examining whether or not a cell is glowing after a certain experiment, which is also observed by employing the fluorescent observation.

In a common microscopic observation, the microscopy observer (noted simply as "observer" hereinafter) first observes as to where a desired specimen exists by using an object lens of a low magnification ratio, followed by observing an enlarged image of the desired specimen by using an object lens of a high magnification ratio. In this event, the magnification ratio of the object lens is low, e.g., 1× at most, making it difficult to find where the desired specimen exists in relation to a specimen retention member such as a well plate and slide glass. Therefore, the observer has been finding out by looking at all over the specimen retention member.

In a transmissive illumination observation for searching for a desired specimen, there are methods available. An image of the entirety of a specimen retention member showing a picture of the specimen is obtained by sticking together images obtained by an object lens of a low magnification ratio and the position of the specimen is identified from the image of the entirety. Or, an image of the entirety of a specimen retention member is obtained by using a macro light path and the position of the specimen is identified from the image of the entirety.

In the fluorescent observation, however, there is much of self fluorescence of the observation optical system such as an object lens and prism, and of the specimen retention member such as a plastic dish. Because of this, it has not been possible to obtain the image of the entirety of the specimen retention member making the position of the specimen within the specimen retention member apparent even if images are stuck together or they are picked up in a macro light path because of the self fluorescence.

Furthermore, various methods for reducing self fluorescence of the observation optical system of a microscope have been proposed; there has not been a consideration of the self fluorescence of a specimen retention member.

Meanwhile, a reference patent document 1 has disclosed a technique equipping a sample holder for a laser microscopic anatomy system with an identification-use code (i.e., a protrusion in a comb form) and a sample holder retention member with a site for recognizing the code, thereby making it possible to identify the sample holder within the laser microscopic anatomy system. The technique aims at automating the process such as assigning cut specimens to individual accommodating containers of a sample holder, thereby carrying out a microscopic anatomy automatically.

Another reference patent document 2 has disclosed a technique constituting a specimen holder comprised by a stage of a microscope by a Petri dish retention unit for retaining a Petri dish and by a slide glass retention unit for retaining a slide glass, enabling a retention of a Petri dish of different sizes by placing a Petri dish retention unit movable in relation to a holder board and retaining the slide glass at a step part equipped in the holder board.

The technique according to the above noted patent document 1, while enabling an automatic operation of the accommodating device based on the code information of the sample holder, is faced with a technical problem of being unable to obtain a whole image with a self fluorescence removed from the sample holder showing a picture of a specimen in a fluorescent observation because the patent document 2 provides no disclosure on a correction of an observation image such as a removal of the self fluorescence of the sample holder.

Likewise, the technique according to the above noted patent document 2, while enabling a retention of various specimen retention members such as a Petri dish and slide glass, does not enable a correction of an observation image, such as a removal of a self fluorescence of the specimen retention member as in the case of the above noted patent document 1. Therefore, the technique is faced with a technical problem of being unable to obtain an image of the entirety with the self fluorescence removed from the specimen retention member showing a picture of a specimen.

Patent document 1: Published Japanese translations of PCT international publication for patent applications 2006-506672

Patent document 2: Laid-Open Japanese Patent Application Publication No. H11-202213

SUMMARY OF THE INVENTION

A purpose of the present invention is to provide a technique enabling an effective obtainment of the whole image of a specimen retention member showing a picture of a specimen without an influence of a self fluorescence of the specimen retention member or optical system in a fluorescent observation using a microscope apparatus.

Another purpose of the present invention is to provide a technique enabling an effective search for an observation region or such operations by using a macro observation image that is the whole image of a specimen retention member showing a picture of a specimen in a fluorescent observation using a microscope apparatus.

A first aspect of the present invention is to provide a control method for a microscope apparatus, comprising: a first step for recognizing a type of a specimen retention member retaining a specimen; a second step for obtaining a first image including the whole image of a specimen retention member showing a picture of the entirety of the specimen retention member and an image of the specimen, and obtaining a second image including only the whole image of the specimen retention member in accordance with the type of the specimen retention member; and a third step for obtaining a macro observation image with a self fluorescence removed except for the specimen based on the first image and second image.

A second aspect of the present invention is to provide a microscope apparatus, comprising: a specimen retention member for retaining a specimen; an observation optical system and image pickup apparatus for obtaining an image of the specimen; and an image processing apparatus for removing a self fluorescent image other than the specimen by using a first image including an image of the specimen obtained at a focused focal point position of an object lens constituting the observation optical system and by using a second image obtained at other than the focused focal point position.

The present invention noted above is contrived, as an example, to identify a type of a specimen retention member and transmit the type information to a control unit of the microscope apparatus. The control unit issues an instruction based on the information, makes an essential microscope drive performed for obtaining the whole image of the specimen retention member and obtains the whole image of the specimen retention member showing a picture of the specimen. Furthermore, a focal point is shifted to a position where the specimen retention member is seen and the specimen cannot be seen based on the instruction of the control unit, and the whole image of the specimen retention member showing no picture of the specimen is obtained. A subtraction of the whole image of the specimen retention member showing no picture of the specimen from the whole image of the specimen retention member showing a picture of the specimen by applying image processing makes it possible to acquire the whole image of the specimen retention member showing a picture of the specimen with little influence of a self fluorescence. This contrivance makes it possible to obtain a whole image (i.e., a macro observation image) of a specimen retention member showing a picture of the specimen effectively in a fluorescent observation.

BRIEF DESCRIPTION OF THE DRAWINGS

FIG. 1 is a side view diagram exemplifying a configuration of an inverted microscope as a preferred embodiment of a microscope apparatus embodying a control method therefor according to the present invention;

FIG. 3 is an exploded diagonal diagram showing an extracted part of an inverted microscope according to a preferred embodiment of the present invention;

FIG. 5 is a block diagram exemplifying a connection relationship of a control system of an inverted microscope according to a preferred embodiment of the present invention;

FIG. 12 is a side view diagram showing a modified embodiment of an inverted microscope according to a preferred embodiment of the present invention;

FIG. 14 is a diagonal view diagram showing a stage of an inverted microscope according to a second preferred embodiment of the present invention; and FIG. 15 is a conceptual diagram exemplifying a configuration of a stage control board of an inverted microscope according to the second embodiment of the present invention.

DESCRIPTION OF THE PREFERRED EMBODIMENTS

The following is a detailed description of the preferred embodiment of the present invention by referring to the accompanying drawings.

First Embodiment

Figure 2:
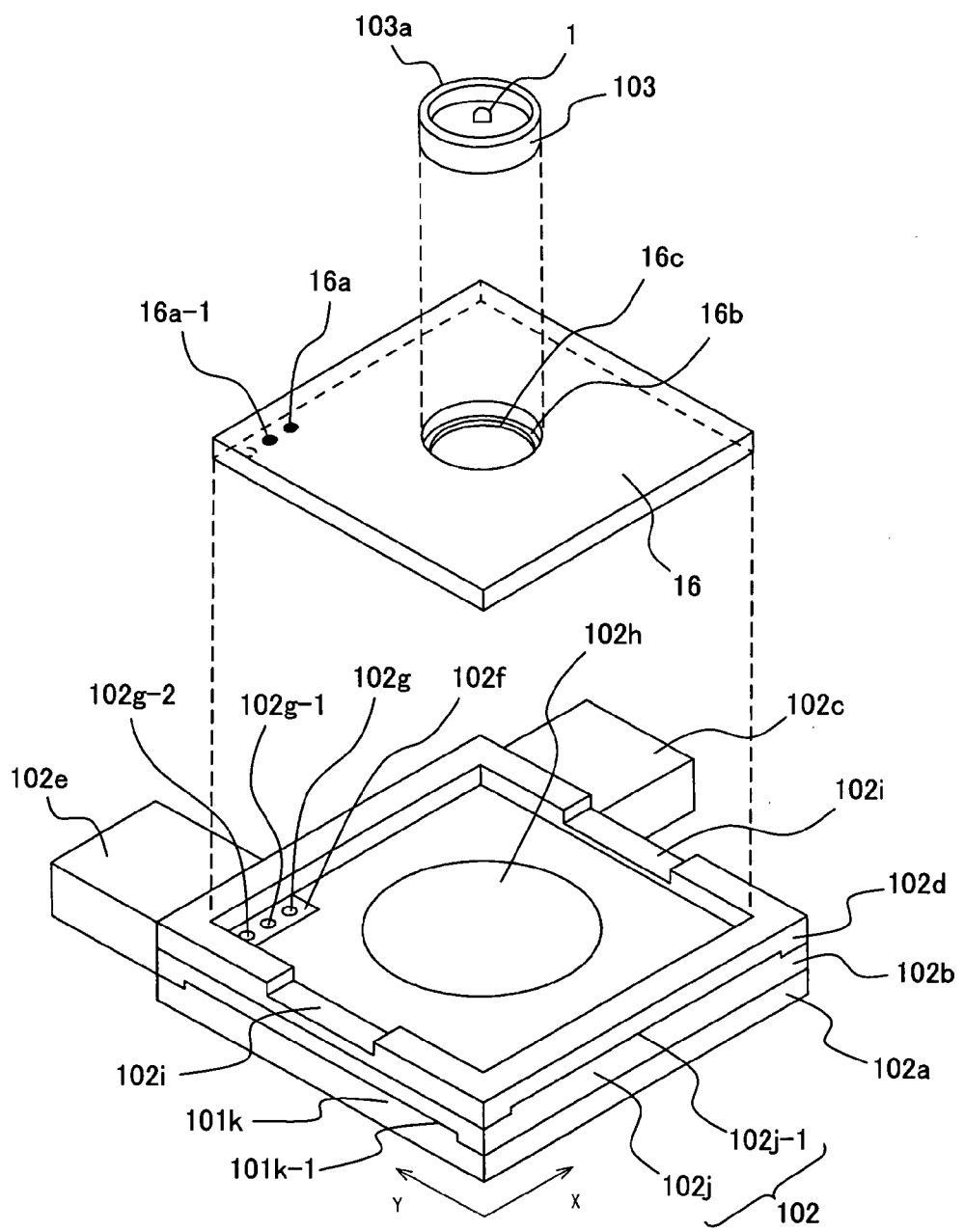
FIG. 2 is an exploded diagonal diagram showing an extracted part of an inverted microscope according to a preferred embodiment of the present invention.

FIG. 1 is a side view diagram exemplifying a configuration of an inverted microscope as a preferred embodiment of a microscope apparatus embodying a control method therefor according to the present invention; while FIGS. 2 and 3 are exploded diagonal diagrams showing an extracted part of an inverted microscope according to the present embodiment.

Referring to FIG. 1, a stage 102 is fixed onto an inverted microscope main body 101 of the inverted microscope 100 according to the present embodiment, with a specimen 1 and such being placed on the stage 102. A configuration is such that an object lens 104 placed under the specimen 1 is stationarily fixed onto a revolver 105 together with object lenses (i.e., the object lenses 104-1 and 104-2 shown in FIG. 1) with different magnification ratios, or such, so as to be placed selectively on the optical axis O by rotating the revolver 105. The object lens 104-1 is configured to be a magnification ratio, e.g., 1×, enabling a low magnification observation.

The revolver 105 is fixed onto a revolver retention table 106 which is connected to a revolution focus unit 107 by way of a rack and pinion mechanism (not shown in a drawing herein) incorporated in the inverted microscope main body 101, and a revolution movement of the revolution focus unit 107 is converted into a linear movement of the revolver retention table 106 in the direction of the optical axis O.

A lamp house 108 has a built-in light source 108a, and an illumination tube 109 retains the lamp house 108 and is stationarily yet detachably attached to the inverted microscope main body 101. An excitation filter 111a, a dichroic mirror 111b and an absorption filter 111c are fixed onto a mirror unit 111d. The mirror unit 111d is configured to be insertable into, and retractable from, the optical axis O within a mirror cassette 111 driven by a motor (not shown in a drawing herein).

The inverted microscope main body 101, comprising a mirror 112 and a relay lens group 113, deflects the light from the specimen imported by the object lens 104 to a lens tube 114. A prism 115 is in the inside of the lens tube 114, deflects the light from the relay lens group 113 and transmits it to an eye piece lens 116. The lens tube 114 is stationarily yet detachably attached to the inverted microscope main body 101.

The inverted microscope main body 101 comprises a transmissive illumination pillar 118, a lamp house 117 and a condenser 119 (i.e., a collector optical system) so that the light beam coming out of a light source 117a of the lamp house 117 is deflected to 90 degrees by a mirror 118a housed in the transmissive illumination pillar 118, led through the condenser 119 and emitted to a Petri dish 103. The condenser 119 is moved by a handle 118b in the up and down directions in terms of the showing of FIG. 1.

The inverted microscope main body 101 is also enabled to eject the light from the object lens 104 to the front direction in terms of the delineation of FIG. 1 through a prism 120 and a hole 121. The prism 120 is configured to be insertable into, and retractable from, the optical axis O by being driven by a motor (not shown in a drawing herein). A cylinder unit 122 is enabled to fix a camera 123 such as a charge-coupled device (CCD) camera. A camera 123 (refer to FIG. 5 described later) is omitted from FIG. 1 for convenience of description.

The stage 102 is configured such that the center thereof moves into the optical axis O at the initialization without an exception and a sensor (not shown in a drawing herein) equipped within the stage 102 recognizes the position of the optical axis O. Therefore, even if the specimen 1 is moved by driving the stage 102, the position in relation to the optical axis O in the X-Y direction (described later) is always recognized by the control apparatus 10.

FIG. 2 shows a detailed example of the stage 102 which comprises a pedestal 102a, a middle stage 102b, a motor 102c and an upper stage 102d.

The pedestal 102a is mounted onto the inverted microscope main body 101. The middle stage 102b is movable in the X direction (per the delineation of the drawing) in relation to the pedestal 102a by means of the motor 102e and a rack and pinion mechanism (not shown in a drawing herein). The upper stage 102d is movable in the Y direction (per the delineation of the drawing) in relation to the middle stage 102b by means of a rack and pinion mechanism (not shown in a drawing herein).

The middle stage 102b is equipped with a guide unit 102j and the upper stage 102d is equipped with a concave part 102j-1 fitting to the guide unit 102j. The pedestal 102a is equipped with a guide 102k, and the middle stage 102b is equipped with a concave part 102k-1 fitting to the guide 102k. Sliding between the respective guide parts and concave parts enables a movement of the middle stage 102b in the X direction and that of the upper stage 102d in the Y direction.

The upper stage 102d, middle stage 102b and pedestal 102a are featured with opening parts 102h which is configured adequately large so as to enable an observation by using the object lens 104 even with all the movement of the upper stage 102d. The upper stage 102d is featured with a concave part 102i, enabling an easy attachment and detachment of a Petri dish holder 16.

The Petri dish holder 16 is featured with an opening part 16c and a step part 16b, enabling an insertion and retention of a Petri dish 103 on which the specimen 1 is placed. The opening part 16c is configured to be large to the extent of not letting the Petri dish 103 fall through. Also, the opening part 16c and step part 16b are configured so that the centers of the stage 102 and Petri dish 103 match with each other when installing the Petri dish holder 16 on the upper stage 102d.

Magnets 16a and 16a-1 are fixed onto the Petri dish holder 16 for identifying the Petri dish 103 to be retained thereby. That is, the present embodiment is configured to have three spots of the fixing position of the magnets so as to constitute three-bit identification information based on the placement of a magnet in either of the spots.

A stage control board 102f comprising hall elements 102g, 102g-1 and 102g-2 which determine a presence or absence of an electric current application (noted as "current application" hereinafter) based on a presence or absence of magnetism of a magnet placed on the Petri dish holder 16.

Pieces of outer shape information of plural specimen retention members as described later are registered in the stage control board 102f, as described later, so as to enable a selection of the outer shape information of a specimen retention member by using the identification information based on the presence or absence of the current application of the respective hall elements.

FIG. 3 shows a well plate 17 and a well plate holder 18. The well plate 17 is featured with a plurality of depressed holes (i.e., wells 17a) for cultivating a specimen 1. A magnet 18a is fixed onto the well plate holder 18. The well plate holder 18 is also featured with an opening part 18c and a step part 18b as in the case of the Petri dish holder 16, thereby enabling an insertion and retention of the well plate 17. The opening part 18c is configured to be so large as not to hide specimen placement-use wells 17a positioned closest to the outer circumference of the well plate 17 to the extent of not letting the well plate 17 drop through. The opening part 18c and step part 18b are also configured such that the center of the stage 102 matches with that of the well plate 17 when the well plate holder 18 is installed on the upper stage 102d.

Figure 4:
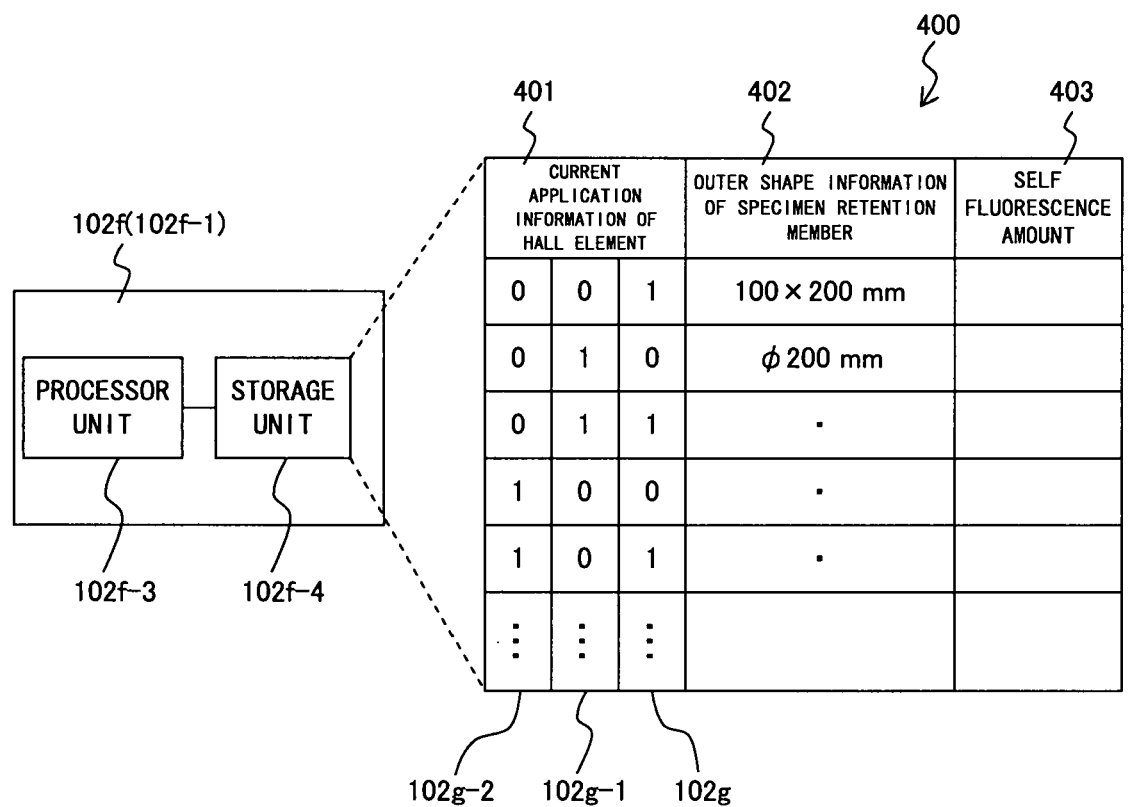
FIG. 4 is a conceptual diagram exemplifying a configuration of a stage control board of an inverted microscope according to a preferred embodiment of the present invention.

As exemplified by FIG. 4, the stage control board 102f of the present embodiment comprises a processor unit 102f-3 and a storage unit 102f-4.

The storage unit 102f-4 stores an outer shape discernment table 400 which stores current application information 401, outer shape information 402, self fluorescence amount 403 and such by correlating them with one another.

The current application information 401 expresses, in one bit, a presence or absence of a current application state of each of the three hall elements 102g, 102g-1 and 102g-2 (i.e., a presence or absence of the magnet 16a of the Petri dish holder 16 and a presence or absence of the well plate holder 18), and is the information showing the type of the Petri dish 103, that of the well plate 17 supported by the well plate holder 18, or the like.

The outer shape information 402 is information indicating outer shapes of the Petri dish 103, well plate 17 and such.

The self fluorescence amount 403 is information indicating respective self fluorescence amounts of the Petri dish 103, well plate 17 and such.

FIG. 5 is a block diagram exemplifying a connection relationship of a control system of the inverted microscope 100 according to the present embodiment. A main body control board 101c placed in the inside of the inverted microscope main body 101 is connected to the control apparatus 10 by way of the cable 10b. A motor (not shown in a drawing herein) of the revolution focus unit 107 is connected to the main body control board 101c by way of a cable (not shown in a drawing herein). Therefore, the control apparatus 10 is capable of rotating the revolution focus unit 107. The control apparatus 10 comprises a storage unit 10e.

Figure 6:
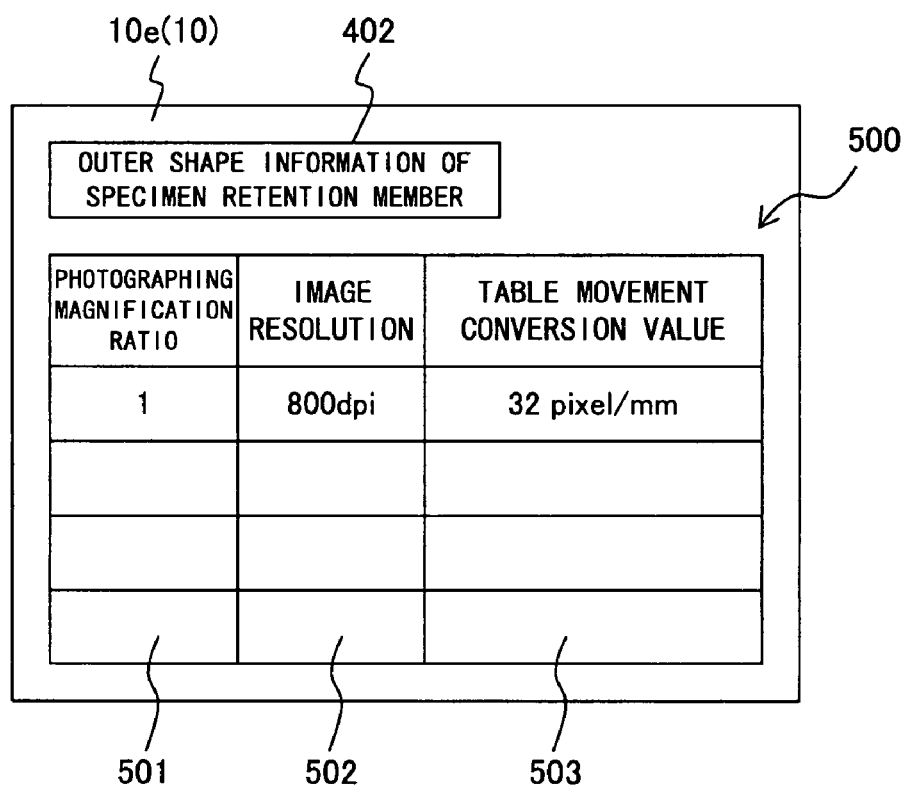
FIG. 6 is a conceptual diagram exemplifying a configuration of a control apparatus of an inverted microscope according to a preferred embodiment of the present invention.

As exemplified by FIG. 6, the storage unit 10e stores information such as the outer shape information 402, a table movement parameter table 500 and such.

The outer shape information 402 is information indicating such as the outer sizes of the specimen retention members such as Petri dish 103 and well plate 17 which are input from the stage control board 102f.

The table movement parameter table 500 stores a photographing magnification ratio 501, an image resolution 502 and a table movement conversion value 503 by correlating with one another.

The main body control board 101*c* is connected to the revolver 105, mirror cassette 111 and prism 120, respectively, by way of cables (not shown in a drawing herein), with each being connected to a motor (not shown in a drawing herein). Therefore, the control apparatus 10 is enabled to drive each motor as in the case of the revolution focus unit 107.

Also, the motor 102*c*, the motor 102*e* and the stage control board 102*f* are connected to the control apparatus 10 by way of a cable 10*a*. Therefore position information of X-Y directions of the stage 102 are transmitted to the control apparatus 10 by way of a cable 10*a*.

The camera 123 and control apparatus 10 are connected to an operation terminal 11 constituting a personal computer (PC) or such by way of a cable 123*a* and a cable 10*c* respectively. The operation terminal 11 has the function of sticking (i.e., joining) together images obtained by using the camera 123. And the camera 123 is connected to the control apparatus 10 by way of a cable 10*d*.

The operation terminal 11 is connected to a monitor 12, a mouse 13, a key board 14 and an image processing apparatus 15, respectively, by way of cables 12*a*, 13*a*, 14*a* and 15*a*, respectively.

Figure 7:
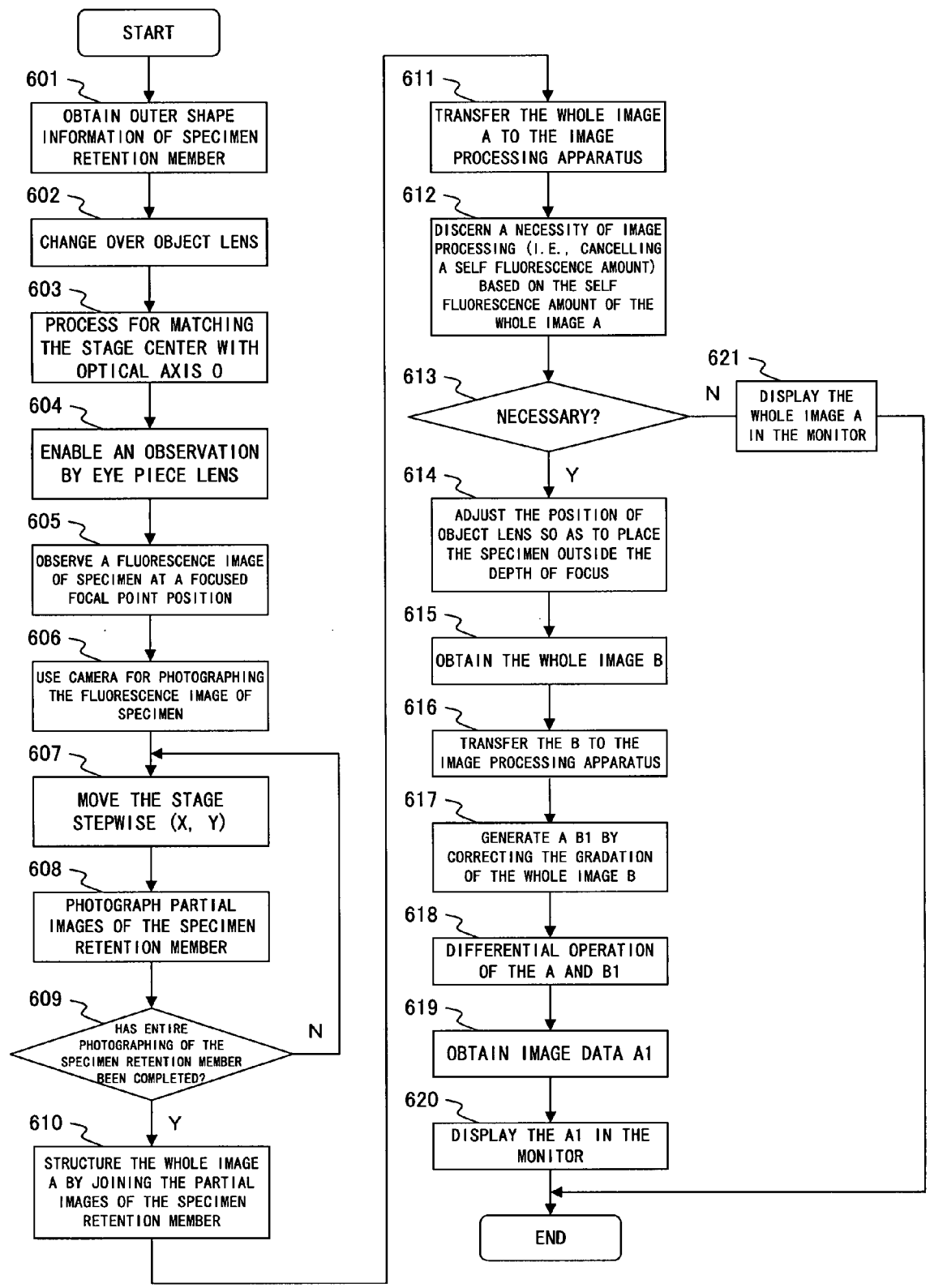
FIG. 7 is a flow chart exemplifying an operation of an inverted microscope according to a preferred embodiment of the present invention.
Figure 8:
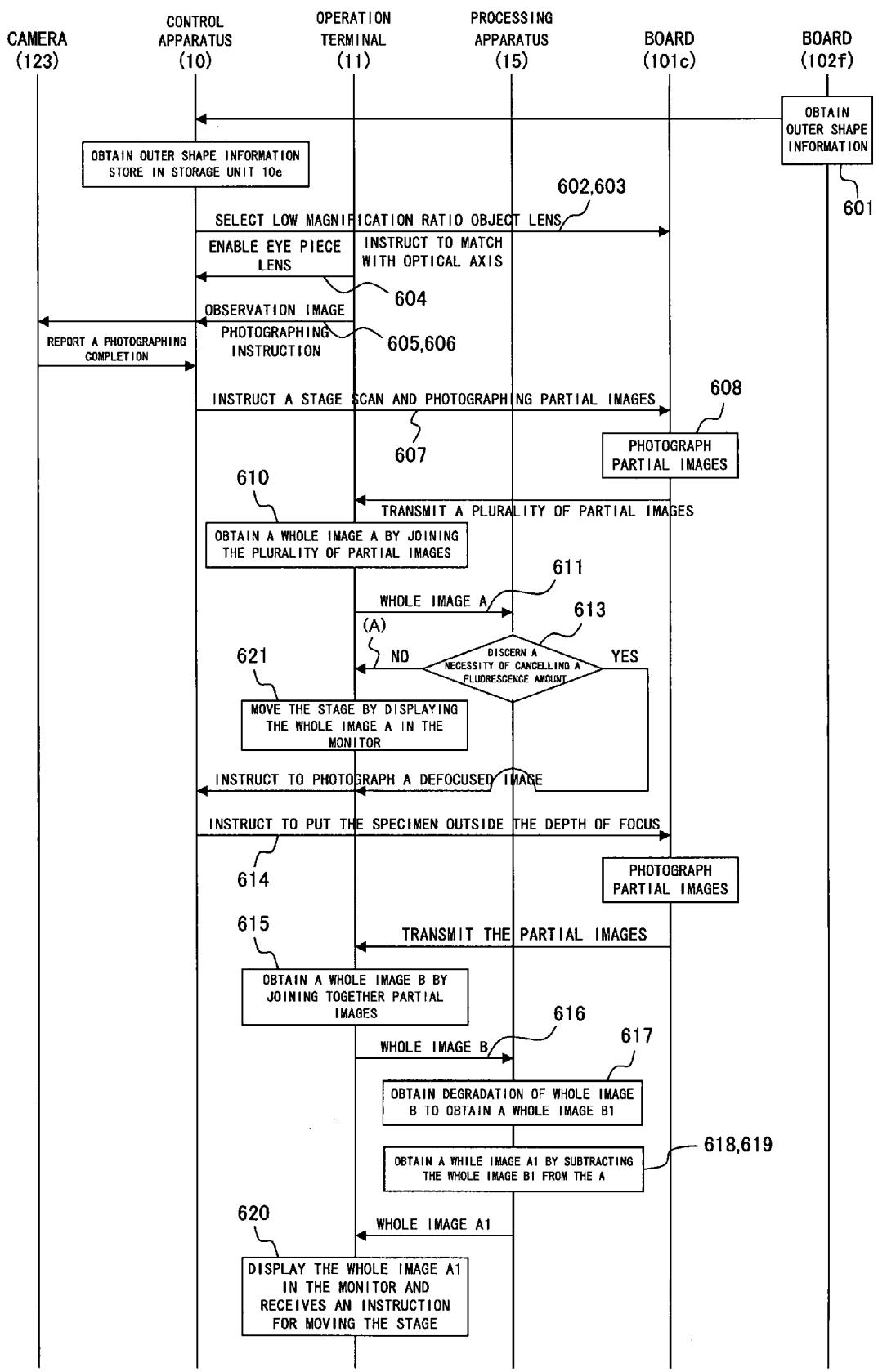
FIG. 8 is a sequence diagram exemplifying an exchange of information among individual constituent components within an inverted microscope according to a preferred embodiment of the present invention.

The next is a description on an example of operations of the present embodiment. FIG. 7 is a flow chart exemplifying an operation of the inverted microscope 100 according to the present embodiment; and FIG. 8 is a sequence diagram exemplifying an exchange of information among individual constituent components within the inverted microscope 100. Note that the sequence chart of FIG. 8 is attached with the corresponding step numbers of the control apparatus 10 as appropriate.

At the time of a microscopy observation, an observer fits a Petri dish 103 into the Petri dish holder 16 and places it on the upper stage 102*d*. In this event, the hall elements 102*g* and 102*g*-1 receives the magnetism of the magnets 16*a* and 16*a*-1. The stage control board 102*f* comprises the storage unit 102*f*-4 and processor unit 102*f*-3, with a correlation table (i.e., the outer shape discernment table 400) of the outer shape information of the specimen retention member corresponding to the current application information of the hall element(s) being input to the storage unit 102*f*-4 before a shipment of the product.

When receiving an input of the current application information (i.e., the current application information 401), the processor unit 102*f*-3 is enabled to refer to the outer shape discernment table 400 of the storage unit 102*f*-4 and output the outer shape information 402 of the specimen retention member. The stage control board 102*f* accordingly selects the outer shape of a Petri dish 103 from the current application information of the hall element and transfer it to the control apparatus 10 (step 601).

The outer shape information of the Petri dish 103 sent to the control apparatus 10 is stored in the storage unit 10*e*, and a scan range of the stage 102 at the time of photographing by the camera (which is described later) is determined on the basis of the outer shape information 402 of the Petri dish 103.

Then, when the outer shape information 402 of the Petri dish 103 is transferred to the control apparatus 10, it rotates the revolver 105 to insert the object lens 104-1 into the optical axis O (step 602). The control apparatus 10 moves the stage 102 so that the center of the stage 102 and Petri dish 103 matches with the optical axis O (step 603). The insertion of the object lens 104-1 into the optical axis O and the movement of the center of the stage 102 to the optical axis O are carried out for every transfer of the outer shape information 402 of a specimen retention member such as the Petri dish 103 to the control apparatus 10.

Then, the observer operates the control apparatus 10 by way of the operation terminal 11 by operating the mouse 13 and key board 14 of the operation terminal 11 and retracts the prism 120 from the optical axis O so as to emit an observation image from the eye piece lens 116 (step 604). The light beam emitted from the light source 108*a* is led through an excitation filter 111*a*, reflected on the dichroic mirror 111*b*, led through the object lens 104-1 and emitted on the specimen 1 housed in the Petri dish 103.

And the fluorescent ray excited in the specimen 1 is led through the object lens 104-1, dichroic mirror 111*b*, absorption filter 111*c* and imaging lens 110, reflected on the mirror 112, led through the relay lens group 113 and prism 115, and observed at the eye piece lens 116 (step 605).

If the specimen 1 is not in a focused focal point position (i.e., a focused position) desired by the observer in this event, the observer operates the control apparatus 10 through the operation terminal 11 by operating the mouse 13 and key board 14, and moves the specimen 1 to the desired focused focal point position by rotating a revolution focus knob 107*a* based on the observer's operating information.

Then the observer inserts the prism 120 into the optical axis by a similar operation as the above description. The observer operates the control apparatus 10 through the operation terminal 11 by operating the mouse 13 and key board 14, and picks up, by using the camera 123, an image of the light from the specimen 1 housed in the Petri dish 103 (step 606).

A signal of a completion of photographing is sent from the camera 123 to the control apparatus 10. The photography completion signal becoming a trigger, the picked-up image data is automatically transferred to the operation terminal 11, and further transferred to the image processing apparatus 15 automatically.

Furthermore, by the photography completion signal, the control apparatus 10 scans the stage 102 automatically in the X and Y directions by a prescribed step width within the scanning range of the stage 102 selected by the storage unit 10*e* (step 607). The step width is a scan step to enable the adjacent images at the time of picking up the images.

Figure 9:
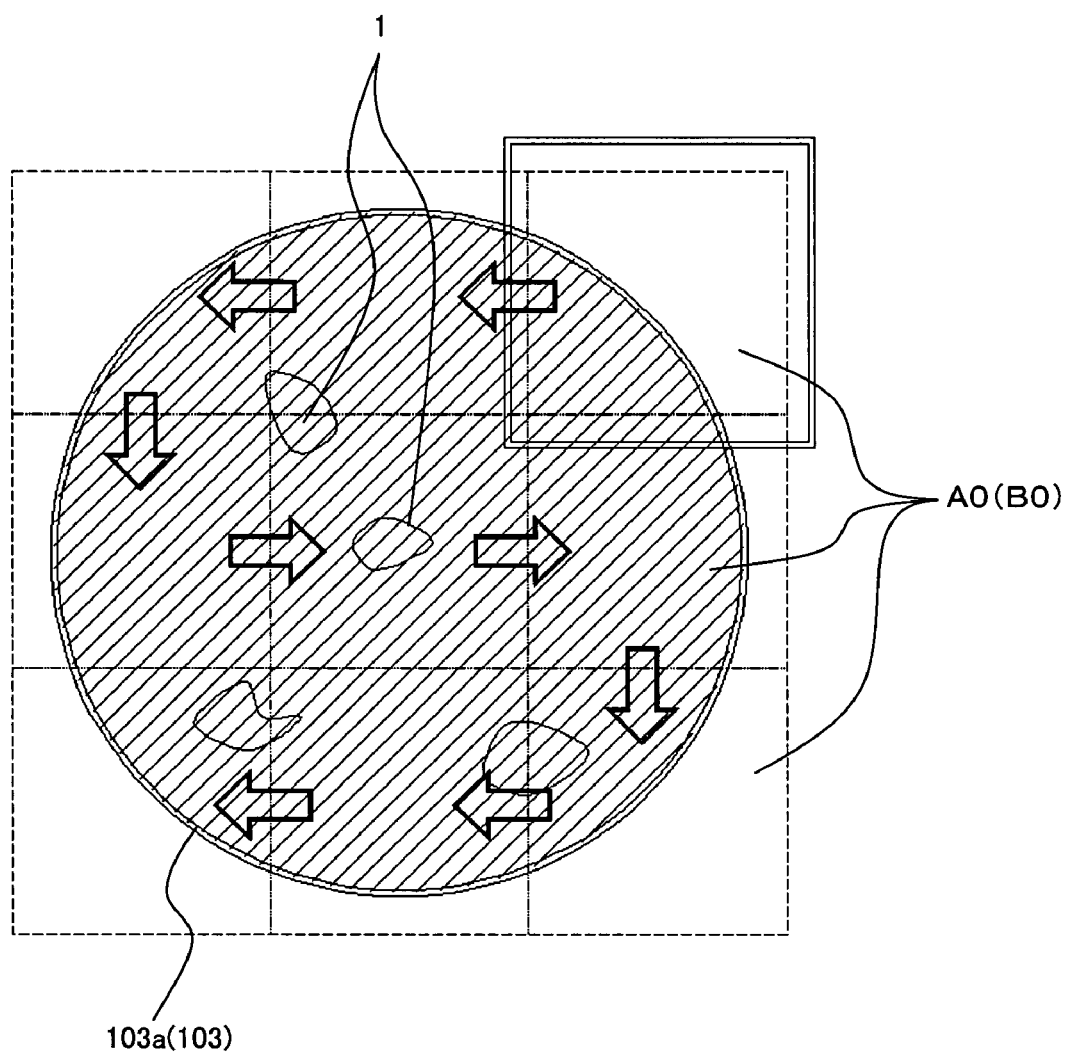
FIG. 9 is a conceptual diagram exemplifying a method for photographing a partial image of a macro observation image in an inverted microscope according to a preferred embodiment of the present invention.

The size of the scan step is determined by the magnification of the object lens 104-1. Therefore, when using the object lens 104-1, how far the distance of moving a position overlaps a pair of images is known, and therefore the size of the scan step is set in the control apparatus at the shipment of a product. Then, partial images A0 are automatically picked up for each scan step as exemplified in FIG. 9 (steps 608 and 609). Then, an image is obtained by joining the partial images A0 for obtaining the whole image of the Petri dish 103. The scan range determined by the outer shape information of the Petri dish 103 is set to a size required for obtaining the whole image of the Petri dish 103.

The opening part 16*c* of the Petri dish holder 16 is configured to be sufficiently large, thereby making it possible to obtain the whole image of the Petri dish 103 by using the object lens 104-1 by means of the scan of the stage 102.

The partial image A0 for each scan step of the stage 102, which has been obtained in the aforementioned process is automatically transferred to the operation terminal 11 and the whole image (i.e., a self fluorescence image) of the Petri dish 103 showing a picture of the specimen 1 by means of the image paste-up function comprised by the operation terminal 11 (step 610). This image is defined as the image data A (i.e., the first image). The image data A is automatically obtained after picking up the initial image.

The image data A is automatically transmitted to the image processing apparatus 15 (step 611).

Figure 10:
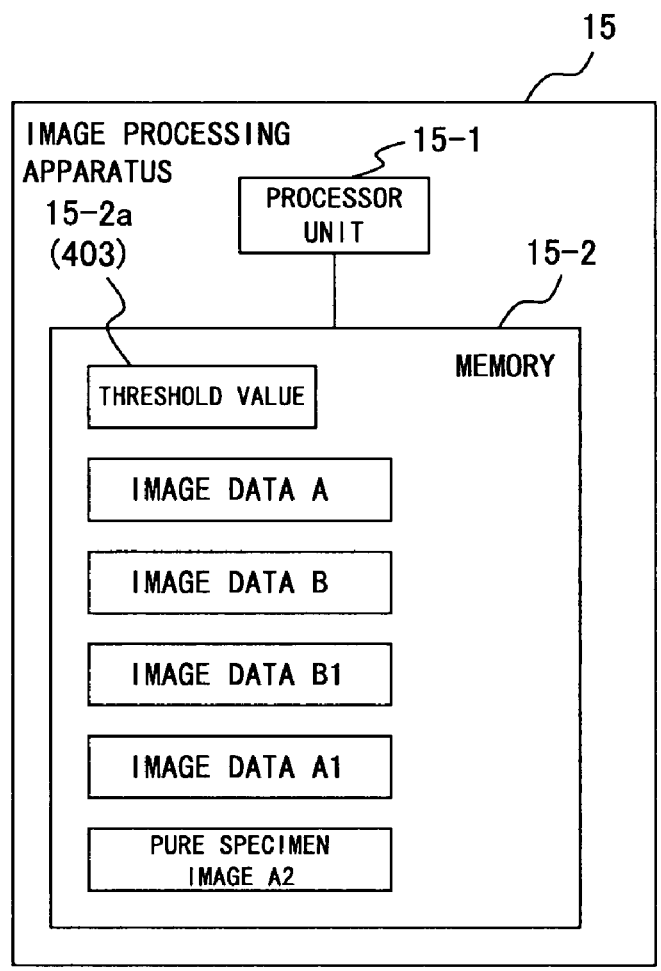
FIG. 10 is a conceptual diagram exemplifying a configuration of an image processing apparatus of an inverted microscope according to a preferred embodiment of the present invention.

As exemplified in FIG. 10, the image processing apparatus 15 according to the present embodiment comprises a processor unit 15-1 and memory 15-2.

The image processing apparatus 15 is capable of applying an image data processing to each of a transmitted plurality of images at the processor unit 15-1. It is also capable of increasing or decreasing the gradation, of image, which is different in each pixel due to a received light intensity. It also sets a threshold value 15-2*a* in the memory 15-2 before the shipment of a product. The present embodiment is configured to set the self fluorescence amount 403 as the threshold value 15-2*a* for judging a necessity of an image data processing depending on the present or absence of a self fluorescence. The maker of the apparatus measure the self fluorescence amount 403 of containers such as the Petri dish 103, well plate 17, and such, and sets the value in the outer shape discernment table 400, followed by setting the value in the threshold value 15-2*a* before the shipment of a product.

Here, the distribution, in the X-Y direction of the stage 102, of a gradation of the self fluorescence of specimen retention members such as the Petri dish 103 and well plate 17 is more gradual than the distribution of the gradation of the specimen in the X-Y direction of the stage 102, and therefore it is possible to compare the self fluorescence of the specimen retention member with the threshold value 15-2*a* even for an image of a specimen retention member such as the Petri dish 103 and well plate 17.

The processor unit 15-1 of the image processing apparatus 15 is capable of judging a necessity of image processing based on the threshold value 15-2*a*. This makes it possible to set so that a differential image data processing (which is described later) is not applied in the case of using a glass dish having a little self fluorescence and that an image data processing is applied in the case of using a plastic dish. Therefore, the image processing apparatus 15 discerns a necessity of image processing based on a difference of the self fluorescence amount 403 of a specimen retention member and applies image processing if needed.

The first is to compare the image data A with the threshold value 15-2*a* set as described above (step 612). If the Petri dish 103 is made of a plastic, the self fluorescence amount of the image data A is large and the image processing apparatus 15 accordingly judges that an image data processing is necessary (step 613). And an instruction of the operation being necessary is transmitted from the image processing apparatus 15 to the control apparatus 10.

Then the control apparatus 10 moves the object lens 104-1 to a position where the specimen 1 is on the outside of the depth of focus thereof (step 614). The observation image of the Petri dish 103 can be seen at the position. The observation image of the Petri dish 103 does not disappear because the thickness of an outer frame part 103*a* and such of the Petri dish 103 in the direction of the optical axis O is sufficiently large as compared to the thickness of the specimen 1 in the direction of the optical axis O. Then, it scans the stage 102 as described above and picks up an image by a camera for each stage scan step, thereby obtaining partial images B0.

Then, images are joined at the operation terminal 11, and the whole image (i.e., a self fluorescence image) of the Petri dish 103 showing a picture of the specimen 1 is obtained. This image data is defined as image data B (i.e., a second image) (step 615). The image data B is obtained entirely automatically. The image data B is obtained with the same exposure time as obtaining the image data A.

Then, the image data B is transmitted to the memory 15-2 of the image processing apparatus 15 (step 616), and image processing are applied to the image data A and image data B.

Figure 11:
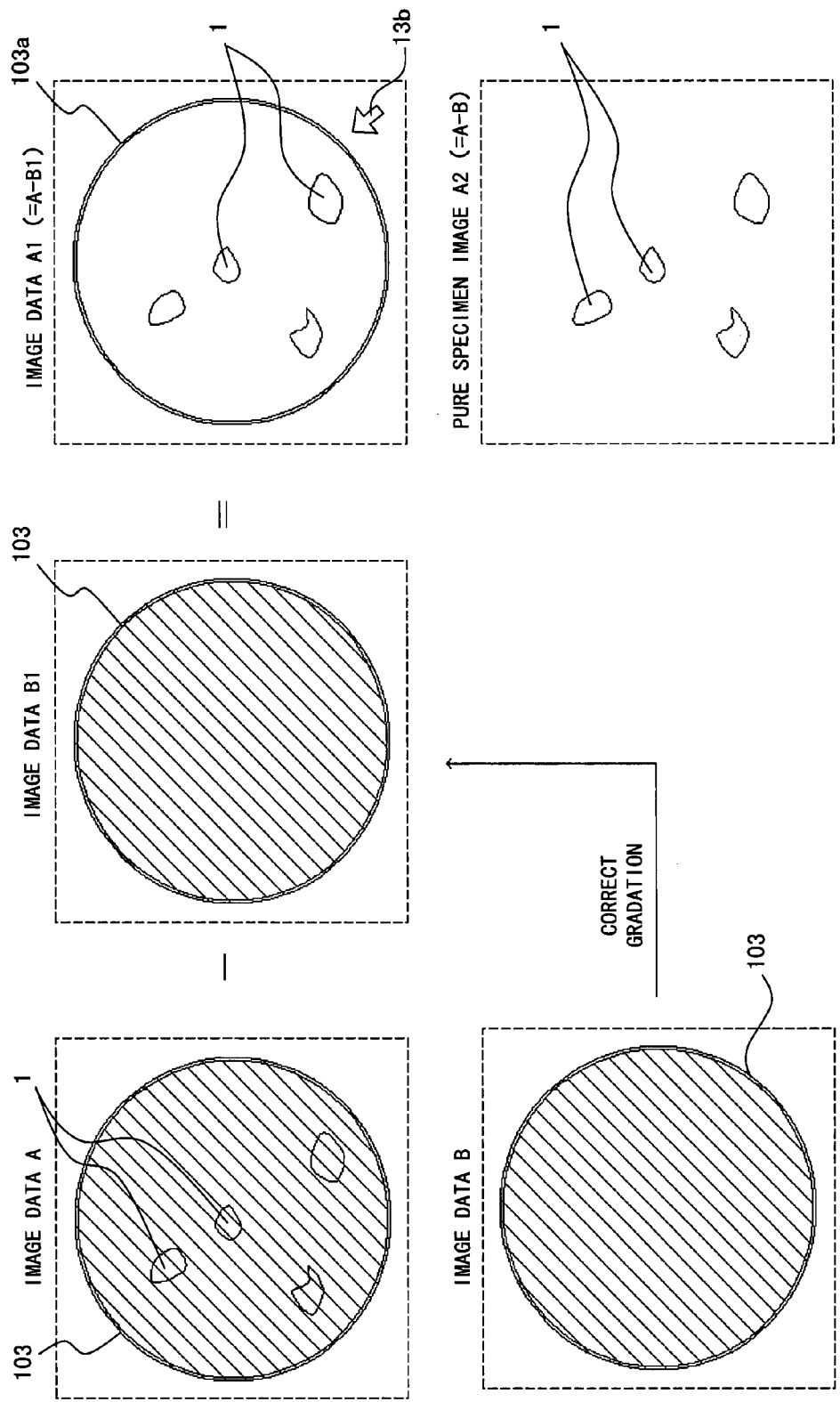
FIG. 11 is a conceptual diagram exemplifying image processing at an image processing apparatus of an inverted microscope according to a preferred embodiment of the present invention.

FIG. 11 is a conceptual diagram exemplifying image processing at the image processing apparatus 15.

The image processing subtracts the image data B (i.e., an image of the Petri dish 103 not showing a picture of a specimen 1) from the image data A (i.e., an image of the Petri dish 103 showing a picture of the specimen 1) at the image processing apparatus 15. Here, a mere subtraction would result in leaving only an image of the specimen 1 (i.e., a pure specimen image A2), and therefore the image processing apparatus 15 generates image data B1 of a result of reducing a gradation of the image data B for each pixel to 95% for example (step 617) and subtracts the image data B1 from the image data A (step 618). This makes it possible to obtain the whole image of the Petri dish 103 showing a picture of the specimen 1 with a 5% gradation of an image of the outer shape (i.e., an outer frame part 103*a*). This image data is defined as image data A1 (i.e., a macro observation image) (step 619).

The image data A1 becomes an image of a result of removing almost all of the optical system such as object lens, prism and such, the self fluorescence of the Petri dish 103 and the dust attached thereto. This accordingly makes it possible to obtain, as the image data A1, the whole image of the Petri dish 103 apparently showing a picture of the position of the specimen 1 in the Petri dish 103.

Then, the image data A1 is transferred to the operation terminal 11 and displayed in the monitor 12 (step 620). This in turn enables the observer to discern as to which part of the Petri dish 103 a specimen exists just by referring to the image data A1. The image data A1 is also obtained entirely automatically.

Here, if the Petri dish 103 is made of glass, in place of made from plastic, then the self fluorescence amount 403 is lower than the set threshold value 15-2*a*, the judgment is that an image data processing is not necessary (step 613), and therefore the operation is not applied to the image data A or image data B. In such a case, an operation after the obtainment of the image data A, such as an obtainment of image data B or such, is not carried out, and instead the image data A, as is, is displayed in the monitor (step 621).

Meanwhile, the inverted microscope 100 according to the present embodiment is configured to transfer positional information of the stage 102 in the X-Y direction without exception to the operation terminal 11 by way of the control apparatus 10. As described above, the positional information of the stage 102 in the X-Y direction expresses a position in relation to the optical axis O. A relationship of a distance (i.e., a table movement conversion value 503) (in millimeters) of the stage 102 in the X-Y direction with the number of pixels of the image data A1 can be obtained on the basis of the relationship of the photographing magnification ratio 501 with the number of pixels (i.e., an image resolution 502) of the image data A1 which are registered in the table movement parameter table 500 in the storage unit 10*e* within the control apparatus 10 as described above.

Accordingly, the pixels of the image data A1 and the movement amount of the stage 102 are transferred to the image processing apparatus 15 based on the positional information of the stage 102 in the X-Y direction and photography magnification ratio information, and a pointer 13*b*, such as an arrow indicating the position of the optical axis O, is overlapped on the image data A1 at the image processing apparatus 15. It is followed by transferring from the image processing apparatus 15 to the operation terminal 11, thereby making it possible to indicate the position of the optical axis O with the pointer 13b in the image data A1 shown in the monitor 12.

If the pointer 13b in the image data A1 displayed in the monitor is moved by using the mouse 13, information of the number of pixels by the movement of the pointer 13b in the image data A1 is transferred to the control apparatus 10. A drive amount of the stage 102 is instructed thereto on the basis of the relationship (i.e., the table movement conversion value 503) of the number of pixels of the image data A1 with a movement amount of the stage 102 in the X-Y direction registered in the storage unit 10e within the control apparatus 10. Also, the positional information of the stage 102 in the X-Y direction can be transferred to the operation terminal 11 by way of the control apparatus 10. Therefore, the movement of the pointer 13b in the image data A1 can be linked with the stage 102.

When observing in a high magnification ratio, the observer determines a position desired to observe by confirming the image data A1. The pointer 13b is moved to the position desired to observe by operating the mouse 13 and key board 14. As described above, the movements of the pointer 13b and the stage 102 are linked together and therefore a position of the Petri dish 103 corresponding to the position specified with the pointer 13b is moved to the optical axis O. In this event, an object lens 104 is inserted into the optical axis O by operating the mouse 13 and key board 14, followed by carrying out an observation.

The next is a description on a microscopic observation using the well plate 17 in place of a Petri dish 103. The well plate 17 is inserted into the well plate holder 18 and it is placed on the upper stage 102d. In this event, the hall element 102g receives the magnetism of the magnet 18a, the stage control board 102f selects the outer shape information 402 of the well plate 17 from the current application information of the hall element and transfers it to the control apparatus 10. The sent outer shape information 402 of the well plate 17 is stored in the storage unit 10e. In this event, a scan range of the stage 102 for a camera photographing is determined from the outer shape information 402 of the well plate 17. Since the opening part 18c of the well plate holder 18 is configured to be sufficiently large, a scan of the stage 102 makes it possible to obtain the whole image of the well plate 17 with the object lens 104-1.

Other than the above, the flow between the above process and an obtainment of the image data A1 is similar to the case of the Petri dish 103 and therefore the description is omitted here.

Incidentally, what is noted as the whole image of a specimen retention member in the above description is, strictly speaking, an image of a lower side opening part (i.e., the opening part 18c of the well plate holder 18 in this case) of the specimen retention member; it is, however, no problem in the usage of confirming the positional relationship of a specimen with the specimen retention member.

This configuration provides the following benefits. The configuration of equipping with a specimen retention member holder such as the Petri dish holder 16 and well plate holder 18 which are specifically for the Petri dish 103 and well plate 17, respectively, of making the lower opening of the specimen retention member holder as much as possible, and of furnishing with the function of joining images such as partial images A0 and partial images B0 makes it possible to obtain the whole image of the specimen retention member (i.e., the image data A and image data B) such as the Petri dish 103 and well plate 17 by using the lower object lens.

It is possible to obtain an image (i.e., image data A1) of a result of removing the self fluorescence of an observation optical system, such as object lens and prism, and of a specimen retention member and removing dust attached thereto through image processing. That is, it is possible to obtain an image of the entirety (i.e., image data A1) of the specimen retention member showing a picture of the position of the specimen 1.

The screening of a specimen retention member of a different outer shape, namely the Petri dish 103 and well plate 17 by selecting the current application information of a hall element which is different for each specimen retention member holder, the correlation table (i.e., the outer shape discernment table 400) showing the relationship of the current application information of the hall element with the outer shape information of the specimen retention member and, from the correlation table, the outer shape information 402 of the specimen retention member, followed by controlling an image pickup procedure, makes it possible to obtain the image (i.e., image data B) of a specimen retention member such as the Petri dish 103 and well plate 17.

A preset of a value of a self fluorescence in the image processing apparatus 15 as a threshold value 15-2a enables the image processing apparatus 15 to discern the difference of self fluorescence amounts of a specimen retention member (i.e., a Petri dish 103) among the glass dish, plastic dish and such, select a necessity of image processing such as "image data A minus image data B1 (i.e., a differential image data processing between the image data A and image data B1) and apply no image processing if not necessary; which contribute to an improvement of efficiency.

A display of the optical axis O of the inverted microscope 100 and an image (i.e., image data A1) after applying image processing to that of a specimen retention member such as the Petri dish 103 and well plate 17, and a linkage of stage 102 with a designation of the position of the optical axis O in relation to the image data A1 enable an effective search of a specimen and a minute observation thereof.

Note that the present embodiment has been described by the case of the Petri dish 103 and well plate 17 as specimen retention member; the same procedure, however, provides a similar benefit in the case of using a specimen retention member such as a slide glass and flask. It has also been described for a method for recognizing a specimen retention member by using a hall element; an alternative method of the code like the bar code etc. recognized in optics is used, or a structure of equipping each specimen retention member holder with a different protrusion may be adopted so that the protrusion presses a piezoelectric element, however. Also alternatively, a configuration of adding an identification unit to a specimen retention member and a stage recognizing the identification may be employed.

Another alternative configuration may be such that the observer inputs type information of a specimen retention member from the operation terminal 11 and an image pickup procedure is controlled on the basis of the information.

Alternatively, in image processing for the case of desiring to display only the specimen in a joined image, while there is no necessity of displaying an image of a specimen retention member, then the image processing may be carried out by changing a setup of the image processing apparatus 15 and using a 100% gradation (i.e., the image data B as is) without reducing the gradation of a subtracting image. In this case, the images of the entirety of the specimen retention member, the self fluorescence of the observation optical system and specimen retention member and the images of dust attached thereto are the same between the subtracting side (i.e., the image data B) and the subtracted side (i.e., the image data A). Therefore, a subtraction of these also makes it possible to obtain the image of only a specimen. The image is defined as a pure specimen image A2 (refer to FIG. 11).

Further conceivable is an image display method using the pure specimen image A2 noted above, as follows. That is, a configuration is such that an outer shape of a specimen retention member and an image (i.e., specimen retention member pseudo image data 510) of an illustrative specimen retention member illustrating holes, a space between holes, and such, are registered and that a selection of the specimen retention member pseudo image data 510 of a specimen retention member from the outer shape information 402 thereof is enabled.

Then, the specimen retention member pseudo image data 510 of the specimen retention member selected when installing it is overlapped again on the pure specimen image A2 obtained by the above noted image processing. By this, a whole image of the specimen retention member, without the image of the self fluorescence and the dust mentioned above, showing an apparent picture of the position of the specimen 1 within the specimen retention member.

Meanwhile, the use of the image (i.e., the image data A1) of the entirety of the specimen retention member of a result of removing the self fluorescence of the observation optical system and specimen retention member and removing the dust attached thereto makes it possible to obtain the information such as the number of (holes of) wells 17a for cultivating a specimen and the distance between the individual wells 17a by recognizing the gradation of the whole image. Furthermore, a transfer of the obtained number of wells 17a and distance information between the wells 17a enables also an image pickup for each well 17a.

FIG. 12 is a side view diagram showing a modified embodiment of the inverted microscope 100 according to the first embodiment. The same component sign is assigned to the same configuration as that of FIG. 1, such as the object lens 104, and the description is omitted in the showing of FIG. 12. Also, the configurations between the relay lens group 113 and eye piece lens 116 are the same as those of FIG. 1; the drawings are omitted for the space of delineation. The inverted microscope main body 101-1 according to the present modified embodiment comprises an observation optical system constituted by an object lens 104-1 of the lowest magnification ratio being approximately 1×, a macro object lens 204 of the lowest magnification ratio being approximately 0.07× and a macro observation optical system constituted by a macro object lens 204-1.

The macro object lens 204 is configured to have a magnification ratio and a numerical aperture so as to photograph the overall image of a Petri dish 103, and the macro object lens 204-1 is configured to have the same so as to photograph the overall image of the well plate 17. The macro object lenses 204 and 204-1 are so placed as to be selectively inserted into the optical axis O by rotating the revolver 105.

A revolver retention table 206 is enabled to move in a straight line in the optical axis direction O-1 by means of a rack and pinion mechanism (not shown in a drawing herein). The revolver 205, revolver retention table 206 and mirror cassette 211 comprise motors (not shown in a drawing herein).

An excitation filter 211a, a dichroic mirror 211b and an absorption filter 211c are fixed in a mirror unit 211d. The mirror unit 211d is configured to be insertable into, and retractable from, the optical axis O-1 within the mirror cassette 211 by means of a motor (not shown in a drawing herein). The mirror cassette 211 also comprises a lens 211f for expanding the light beam of the illumination light from a light source 108a.

The inverted microscope main body 101-1 comprises an imaging lens 210 and a mirror 212b, and is enabled to emit the light from the specimen 1 imported by the macro object lens 204 to a prism 120-1. The prism 120-1 is enabled to deflect the light from the mirror 212b to the direction of coming off the drawn paper shown in FIG. 12. Further, the inverted microscope main body 101-1, comprising a prism 120-2, is enabled to deflect the light from the mirror 212b to the direction of a mirror 112. The prisms 120, 120-1 and 120-2 are fixed in the same prism unit which also comprises a motor (not shown in a drawing herein). The mirror 212a enables an observation of an observation image from an object lens 104 and from a macro object lens 204 by an eye piece lens.

A stage 102-1 is capable of moving the entire circumference of the well plate 17 with the optical axis O and optical axis O-1 as the respective center.

Figure 13:
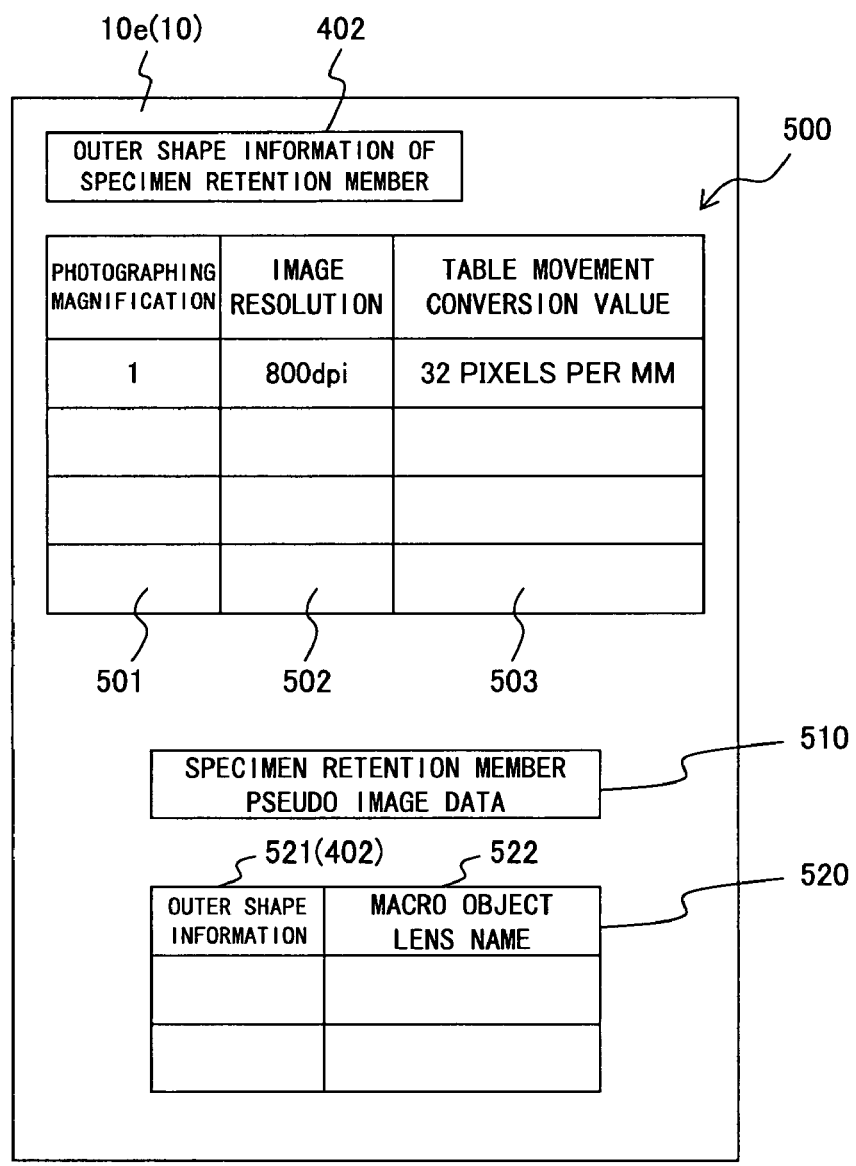
FIG. 13 is a conceptual diagram exemplifying a modified embodiment of a control apparatus of an inverted microscope according to a preferred embodiment of the present invention.

As exemplified by FIG. 13, the present modified embodiment is configured in a manner that a storage unit 10e stores a macro object lens registration table 520 and specimen retention member pseudo image data 510 in addition to the above described outer shape information 402 and table movement parameter table 500.

The specimen retention member pseudo image data 510 is contour image data of the Petri dish 103 and well plate 17, and is used for synthesizing to an image of the specimen 1 as described above.

The macro object lens registration table 520 stores outer shape information 521 (i.e., the outer shape information 402) and a macro object lens name 522 by correlating with each other, and registers a macro object lens 204 to be used for photographing the whole image in accordance with the size of the Petri dish 103, well plate 17 and such, as described later.

That is, the macro object lens registration table 520 sets information as to which macro object lens (i.e., the macro object lens name 522) is to be inserted into the optical axis O-1 for each piece of outer shape information (i.e., outer shape information 521 and outer shape information 402) of specimen retention members.

The connection of the control system according to the present embodiment is configured as follows. Respective motors (not shown in a drawing herein) of the revolver 205, revolver retention table 206, mirror cassette 211 and prism unit are connected to a main body control board 101c by way of cables.

At the time of a microscopic observation, the observer fits the Petri dish 103 into the Petri dish holder 16 and put it on an upper stage 102d. The outer shape information 402 of the Petri dish 103 is stored in the storage unit 10e of the control apparatus 10 as in the case of the first embodiment. The control apparatus 10 makes the macro object lens 204 inserted into the optical axis O-1 based on the type information (i.e., the macro object lens name 522) of a macro object lens selected at the storage unit 10e. And, the outer shape information 402 of the Petri dish 103 having been transferred to the control apparatus 10, it moves the center of the stage 102 to the optical axis O-1. The control apparatus 10 also retracts the mirror unit 111d from the optical axis O-1 so as to illuminate the light from the light source 108a to the lens 211f. The selection of a macro object lens, the insertion of the selected macro object lens into the optical axis O-1, the movement of the center of the stage 102 to the optical axis O-1 and the retraction of the mirror unit 111d are carried out by referring to the macro object lens registration table 520 at every time of transferring the outer shape information of a specimen retention member to the control apparatus 10.

Then, the observer operates the control apparatus 10 by way of the operation terminal 11 by operating the mouse 13 and key board 14 and inserts the prism 120-2 into the optical axis O so as to emit an observation image to the eye piece lens 116. The light beam coming out of the light source 108*a* goes through the excitation filter 211*a*, gets reflected on the dichroic mirror 211*b*, goes through the macro object lens 204 and illuminates the specimen 1 housed in the Petri dish 103.

Then, the fluorescence excited in the specimen 1 goes through the macro object lens 204, dichroic mirror 211*b*, absorption filter 211*c* and imaging lens 210, followed by being reflected on the mirror 212*b*, prism 120-2, mirror 112 and mirror 212*a*, going through the relay lens group 113 and prism 115, and is observed at the eye piece lens 116.

If the specimen 1 is not at a focused point position desired by the observer, she/he operates the control apparatus 10 by way of the operation terminal 11 by operating the mouse 13 and key board 14 so that the revolver retention table 206, revolver 205 and macro object lens 204 are moved in the optical axis O-1 direction based on the information, and moved to the focused focal point position desired by the observer.

Then, the prism 120-1 is placed on the optical axis O by the operation as described above. The observer operates the control apparatus 10 by way of the operation terminal 11 by operating the mouse 13 and key board 14 and picks up image of the light from the specimen 1 housed in the Petri dish 103 with the camera 123. In this event, a signal of a photographing being completed (noted as "photography completion signal" hereinafter) is sent from the camera 123 to the control apparatus 10. With the photography completion signal being used as trigger, the pickup image data is automatically transferred to the operation terminal 11, and further to the image processing apparatus 15 automatically. This makes it possible to obtain a whole image of the Petri dish 103 showing a picture of the specimen 1. This image is defined as image data A.

Then, the macro object lens 204 is moved to a position where the specimen 1 is on the outside of the depth of focus on the macro object lens 204. At this position, an observation image of the Petri dish 103 can be seen. Since the thickness of the specimen retention member in the optical axis direction O-1 is sufficiently large as compared to the thickness of the specimen 1 in the optical axis direction O-1, the observation image of the Petri dish 103 does not disappear. Therefore, it is possible to obtain a whole image of the Petri dish 103 not including the specimen 1. This image data is defined as image data B. The image data B is entirely obtained automatically.

The flow hereafter until an obtainment of image data A1 is similar to the case of the first embodiment and therefore the description is omitted here. After obtaining the image data A1, the operation terminal 11 transmits A1 image obtainment information, meaning that the image data is obtained, to the control apparatus 10. Having received the A1 image obtainment information, the control apparatus 10 moves the center of the stage 102 to the optical axis O.

If the specimen retention member is a glass dish, A1 image un-obtainment information, meaning that image processing is not applied due to a threshold value, is transferred to the control apparatus 10. Having received the A1 image un-obtainment information, the control apparatus 10 moves the center of the stage to the optical axis O. Operations after the obtainment of the image data A, such as an obtainment of image data B, are not carried out and instead the image data A is displayed as is in the monitor 12.

Also the same as the first embodiment is a case of observing at a higher magnification ratio, and the description is accordingly omitted herein.

The next is a description of a microscopic observation when using a well plate 17 in place of the Petri dish 103. The observer inserts the well plate 17 into the well plate holder 18 and places it on the upper stage 102*d*. The outer shape information 402 of the well plate 17 is transmitted to the control apparatus 10 as in the case of the first embodiment. The control apparatus 10 inserts the macro object lens 204-1 into the optical axis O-1 based on the type information of a macro object lens selected in the macro object lens registration table 520 of the storage unit 10*e* comprised by the control apparatus 10.

The flow hereafter until an obtainment of image data A1 is similar to the above described, and therefore the description is omitted herein.

Such a configuration of the modified embodiment provides the following benefits. A whole image (i.e., the image data A and image data B) of a specimen retention member can be obtained without joining images. This provides higher reliability of a whole image than that of a joined image. Other benefits are similar to the case of the first embodiment.

Meanwhile, the present modified embodiment is configured to use a plurality of macro object lenses for obtaining a whole image of a specimen retention member of the Petri dish 103, the well plate 17; a use of a combination of a single macro object lens and a variable magnification optical system may apply, however. And, when obtaining an image of a specimen retention member not including an image of the specimen 1, the present modified embodiment is configured to move the revolver retention table 206; alternatively, however, a camera 123 comprising a mechanism for moving the revolver retention table 206 in the direction perpendicular to the drawing of FIG. 12 may be moved on the basis of an instruction from the control apparatus 10, thereby obtaining an image of the specimen retention member not including an image of the specimen 1.

Second Embodiment

FIG. 14 is a diagonal view diagram showing a stage of an inverted microscope according to a second preferred embodiment of the present invention. In the showing of FIG. 14, the pedestal 102*a*, middle stage 102*b* and such are the same configuration as those described for the first embodiment, and therefore a duplicate description is omitted herein.

A stage 102 according to the present embodiment is configured to provide an upper stage 102*d* with a specimen retention member discernment mechanism 300 comprising a piezoelectric element in which an output voltage is changed by a shift amount of insertion or retraction, in the longitudinal direction, of an axially movable shaft 301.

The specimen retention member discernment mechanism 300 has a built-in elastic body such as a spring, thus always pressing the shaft 301 toward the center of an opening part 102*h*. The specimen retention member discernment mechanism 300 and shaft 301 are provided with respective key grooves (not shown in a drawing herein) so as to prevent the shaft 301 from rotating.

The tip of the shaft 301 is featured with a specimen retention part 302, with a projection part 303 being featured on the lower part of a specimen retention surface. The specimen retention member discernment mechanism 300, shaft 301 and specimen retention part 302 are equipped in two positions opposite to each other across the center of the stage 102, thereby making it possible to sandwich a specimen retention member such as the Petri dish 103 and well plate 17.

The specimen retention member discernment mechanism 300 is connected to a stage control board 102*f*-1 by way of a cable (not shown in a drawing herein), and the stage control board 102*f*-1 is connected to the control apparatus 10 by way of a cable 10*a*. The stage control board 102*f*-1 comprises a processor unit 102*f*-3 and a storage unit 102*f*-4 likewise the stage control board 102*f* exemplified in the above described FIG. 4.

And plural pieces of outer shape information of plural specimen retention members are registered in a storage unit 102*f*-4 of the stage control board 102*f*-1 as an outer shape discernment table 530 as exemplified in FIG. 15. The outer shape discernment table 530 stores outer shape information 532 (i.e., outer shape information 402) and a voltage value 531 generated by a shift-to-voltage (electric signal) conversion element, such as a piezoelectric element of the specimen retention member discernment mechanism 300, in response to a shift amount of the shaft 301 moving in and out in relation to the outer size of an individual Petri dish 103 and well plate 17, by correlating with each other.

Then, the piezoelectric element comprised by the specimen retention member discernment mechanism 300 generates a voltage in response to the pressing force (i.e., a shift amount) of the shaft 301 so as to transmit a voltage value 531 to the stage control board 102*f*-1, thereby making it possible to select the outer shape information 532 (i.e., outer shape information 402) of a specimen retention member, according to the configuration.

At a microscopic observation, the observer matches the center of the Petri dish 103 approximately with the center of the opening part 102*h* and, while pressing the shaft 301 toward the opposite to the center of the opening part 102*h*, places the Petri dish 103 on the left and right projection parts 303. In this event, the shafts 301 are always pressed toward the center of the opening part 102*h*, thereby making it possible to retain the Petri dish 103 without allowing it to drop.

The piezoelectric element within the specimen retention member discernment mechanism 300 generates a voltage in relation to a pressure amount (i.e., a press-in amount) of the shaft 301 against the specimen retention member discernment mechanism 300 and transmits a voltage value 531 to the stage control board 102*f*-1.

Having received an input of the voltage value 531 of the piezoelectric element of the specimen retention member discernment mechanism 300 as described above, the processor unit 102*f*-3 is enabled to refer to the correlation table (i.e., the outer shape discernment table 530) between the voltage value of the piezoelectric element and the outer shape information 532 of a specimen retention member stored in the storage unit 102*f*-4 and output the outer shape information 532 (i.e., the outer shape information 402) of the specimen retention member. Therefore, the stage control board 102*f*-1 selects the outer shape information 532 (i.e., the outer shape information 402) of the Petri dish 103 based on the voltage values 531 of the respective piezoelectric elements of the specimen retention member discernment mechanism 300 and transfer the outer shape information 532 to the control apparatus 10. The transferred outer shape information 402 of the Petri dish 103 is stored in the storage unit 10*e*.

The operation after this process is similar to the case of the first embodiment, and therefore the description is omitted herein.

When using a well plate 17 in place of the Petri dish 103, the operation is also similar to one described above, in which the center of the well plate 17 is matched approximately with that of the opening part 102*h* and, while the shafts 301 are pressed opposite to the center of the opening parts, the well plate 17 is placed on the left and right projection parts 303. The operation thereafter is similar to that of the case of the Petri dish 103, and therefore the description is omitted herein.

The configuration of the stage 102 in the inverted microscope according to the present embodiment provides the following benefits. That is, outer shape information 532 of a specimen retention member, such as the Petri dish 103 and well plate 17, is discerned by referring to the outer shape discernment table 530 that is a correlation table between the voltage value of a piezoelectric element and outer shape information of a specimen retention member based on the voltage value 531 output from the piezoelectric element of the specimen retention member discernment mechanism 300, thereby selecting the outer shape information 532 of the specimen retention member from the outer shape discernment table 530, in addition to the same benefits provided by the first embodiment. This configuration makes it possible to configure an inverted microscope 100 at low cost without a necessity of providing a holder such as the Petri dish holder 16 and well plate holder 18 for each of the specimen retention members.

The benefits provided by the above described individual embodiment of the present invention are listed as follows:

(1) Enabled to obtain a specimen image of a result of removing, by image processing, the self fluorescence of the observation optical system and specimen retention member of a microscope and removing the dust attached to the specimen retention member;

(2) Enabled to obtain a specimen image of a result of removing, by image processing, the self fluorescence of the observation optical system and specimen retention member of a microscope and removing the dust attached to the specimen retention member effectively as a result of applying the image processing using an image not showing a picture of the specimen, in addition to the benefit of the above paragraph (1);

(3) Enabled to obtain an image of the entirety of a specimen retention member showing a picture of the specimen, in addition to the benefit of the above paragraph (1);

(4) Enabled to obtain an image of the entirety of a specimen retention member effectively as a result of driving a microscope automatically on the basis of a result of identifying the type of the specimen retention member, in addition to the benefit of the above paragraph (3);

(5) Enabled to obtain the benefit of a capability of constituting a microscope apparatus inexpensively as a result of not equipping identification means, in addition to the benefit of the above paragraph (3). Also enabled to provide high versatility because of a capability of an easy response even if a new type of specimen retention member in place of the already known;

(6) Enabled to discern whether or not the amount of self fluorescence is large and omit image processing because the image processing is not necessary if the amount is small, thereby enabling an observer to perform the observation more effectively;

(7) Enabled to eliminate an error at the time of joining images and accordingly provide a high reliability of image because the whole image of the specimen retention member is not a joined image, in addition to the benefit of the above paragraph (3);

(8) Enabled to obtain the benefit of a capability of constituting a microscope apparatus inexpensively as a result of not using a specimen retention member holder, in addition to the benefit of the above paragraph (4); and (9) Enabled to obtain the benefit of a capability of constituting a microscope apparatus more inexpensively as a result of using a sensor in place of an identification unit which has been eliminated, in addition to the benefit of the above paragraph (4).

Note that the present invention can apparently be changed in various manners possible with the scope thereof, in lieu of being limited to the configurations exemplified in the embodiment described above.

The present invention is contrived to enable an effective obtainment of a whole image of a specimen retention member showing a picture of a specimen without being influence by a self fluorescence of the specimen retention member, optical system or such, in a fluorescent observation using a microscope apparatus.

It is also contrived to enable an effective search of an observation region by using a macro observation image that is a whole image of a specimen retention member showing a picture of a specimen in a fluorescent observation using a microscope apparatus.

What is claimed is:

1. A control method for a microscope apparatus, comprising:
    a first step for recognizing a type of a specimen retention member retaining a specimen;
    a second step for obtaining a first image including a whole image of a specimen retention member showing a picture of the entirety of the specimen retention member and an image of the specimen, and obtaining a second image including only a whole image of the specimen retention member in accordance with the type of the specimen retention member; and
    a third step for obtaining a macro observation image with a self fluorescence removed except for the specimen based on the first image and second image.

2. The control method for a microscope apparatus according to claim 1,
    obtaining the first image at a focused focal point position of an observation optical system for the specimen and the second image in a state of placing the specimen on the outside of the depth of focus of the observation optical system in the second step.

3. The control method for a microscope apparatus according to claim 1,
    constructing the first and second images by joining a plurality of partial images obtained by the observation optical system in the second step.

4. The control method for a microscope apparatus according to claim 1,
    obtaining the first and second images by using a macro optical system, as observation optical system, of a magnification ratio capable of obtaining the whole image of the specimen retention member at once in the second step.

5. The control method for a microscope apparatus according to claim 1,
    obtaining the macro observation image including a contour image of the specimen retention member and an image of the specimen from the difference between the first image and the second image of a result of correcting a gradation, in the third step.

6. The control method for a microscope apparatus according to claim 1,
    obtaining the macro observation image by synthesizing a simulative contour image of the specimen retention member with a pure specimen image including only an image of the specimen which has been obtained as the difference between the first image and second image, in the third step.

7. The control method for a microscope apparatus according to claim 1, further comprising
    a fourth step for presenting a user with the macro observation image, and moving a position specified by a pointer within the present macro observation image to the optical axis of an observation optical system.

8. A microscope apparatus, comprising:
    a specimen retention member for retaining a specimen;
    an observation optical system and image pickup apparatus for obtaining an image of the specimen; and
    an image processing apparatus for removing a self fluorescent image other than the specimen by using a first image including an image of the specimen obtained at a focused focal point position of an object lens constituting the observation optical system and by using a second image obtained at other than the focused focal point position.

9. The microscope apparatus according to claim 8, wherein
    the second image is obtained in a state of the specimen existing at a position on the outside of the depth of focus of the object lens.

10. The microscope apparatus according to claim 8, wherein
    the first and second images include the whole image of a specimen retention member showing a picture of the entirety of the specimen retention member.

11. The microscope apparatus according to claim 10, further comprising
    identification means for identifying the type of the specimen retention member, and
    control means for controlling the operations for obtaining the first and second images including the whole image of the specimen retention member in the observation optical system based on the identification result of the identification means.

12. The microscope apparatus according to claim 10, further comprising
    an input unit for inputting a type of the specimen retention member, and
    control means for controlling the operations for obtaining the first and second images including the whole image of the specimen retention member in the observation optical system based on an input result of the input unit.

13. The microscope apparatus according to claim 11,
    obtaining the first and second images by means of the image pickup apparatus by moving an object lens of the observation optical system by means of the control means.

14. The microscope apparatus according to claim 8, wherein
    the image processing apparatus comprises a judgment function for comparing a gradation of the first image obtained at a focused focal point position with a predetermined threshold value and judging a necessity of an image data processing for the second image in order to remove the self fluorescent image.

15. The microscope apparatus according to claim 10, wherein
    the first and second images including the whole image of the specimen retention member is constructed by joining a plurality of partial images obtained by the image pickup apparatus.

16. The microscope apparatus according to claim 8, wherein the observation optical system is a macro optical system capable of obtaining the first and second images including the whole image of the specimen retention member at once, and the first and second images including the whole image of the specimen retention member are obtained by using the macro optical system and image pickup apparatus.

17. The microscope apparatus according to claim 11, wherein
the identification means comprises an identification unit which is equipped in a specimen retention member holder supporting each of the specimen retention members and which is unique for each of the aforementioned specimen retention members, and
a recognition unit, being equipped in a holder retention member retaining the specimen retention member holder, for recognizing the identification unit.

18. The microscope apparatus according to claim 11, wherein
the identification means comprises
an identification unit which is equipped in a specimen retention member and which is unique to each of the present specimen retention member, and
a recognition unit, being equipped in a microscope stage placing the specimen retention member, for recognizing the identification unit.

19. The microscope apparatus according to claim 11, wherein
the identification means is a sensor which is equipped in a stage unit placing the specimen retention member and which detects the size of the present specimen retention member, thereby identifying the type thereof.

20. The microscope apparatus according to claim 11, wherein
the control means comprises
a changeover unit for changing over a plurality of object lenses constituting the observation optical system,
a microscope stage for supporting the specimen retention member, and
a focus unit for moving the object lens in the optical axis direction.

21. The microscope apparatus according to claim 12,
obtaining the first and second images by means of the image pickup apparatus by moving an object lens of the observation optical system by means of the control means.

22. The microscope apparatus according to claim 12, wherein
the control means comprises
a changeover unit for changing over a plurality of object lenses constituting the observation optical system,
a microscope stage for supporting the specimen retention member, and
a focus unit for moving the object lens in the optical axis direction.

* * * * *